(12) United States Patent
Pena et al.

(10) Patent No.: US 7,700,563 B2
(45) Date of Patent: *Apr. 20, 2010

(54) SYNTHETIC HEPARIN-BINDING FACTOR ANALOGS

(75) Inventors: Louis A. Pena, Poquott, NY (US); Paul O. Zamora, Gaithersburg, MD (US); Xinhua Lin, Plainview, NY (US); John D. Glass, Shoreham, NY (US)

(73) Assignees: BioSurface Engineering Technologies, Inc., Rockville, MD (US); Brookhaven Science Associates, Upton, NY (US)

(*) Notice: Subject to any disclaimer, the term of this patent is extended or adjusted under 35 U.S.C. 154(b) by 873 days.

This patent is subject to a terminal disclaimer.

(21) Appl. No.: 10/644,703

(22) Filed: Aug. 19, 2003

(65) Prior Publication Data

US 2004/0087505 A1    May 6, 2004

Related U.S. Application Data

(63) Continuation-in-part of application No. 10/224,268, filed on Aug. 20, 2002, now Pat. No. 7,166,574.

(51) Int. Cl.
    A61K 38/00    (2006.01)
    A61K 31/727   (2006.01)
    A61K 38/24    (2006.01)
    C07K 14/00    (2006.01)
    C07K 16/00    (2006.01)
    C08H 1/00     (2006.01)

(52) U.S. Cl. .................. 514/18; 514/56; 530/300; 530/397; 530/399; 530/402

(58) Field of Classification Search ............ None
See application file for complete search history.

(56) References Cited

U.S. PATENT DOCUMENTS

| | | | |
|---|---|---|---|
| 3,272,204 A | 9/1966 | Artandi et al. | |
| 4,172,128 A | 10/1979 | Thiele et al. | |
| 4,193,138 A | 3/1980 | Okita | |
| 4,563,350 A | 1/1986 | Nathan et al. | |
| 4,747,848 A | 5/1988 | Maini | |
| 4,842,575 A | 6/1989 | Hoffman, Jr. et al. | |
| 5,108,436 A | 4/1992 | Chu et al. | |
| 5,197,977 A | 3/1993 | Hoffman, Jr. et al. | |
| 5,509,899 A | 4/1996 | Fan et al. | |
| 5,510,418 A | 4/1996 | Rhee et al. | |
| 5,563,046 A | 10/1996 | Mascarenhas et al. | 435/69.52 |
| 5,608,035 A | 3/1997 | Yanofsky et al. | 530/324 |
| 5,635,597 A | 6/1997 | Barrett et al. | 530/327 |
| 5,643,873 A | 7/1997 | Barrett et al. | 514/12 |
| 5,648,458 A | 7/1997 | Cwirla et al. | 530/324 |
| 5,650,234 A | 7/1997 | Dolence et al. | |
| 5,654,276 A | 8/1997 | Barrett et al. | 514/413 |
| 5,665,114 A | 9/1997 | Weadock et al. | |
| 5,668,110 A | 9/1997 | Barrett et al. | 514/13 |
| 5,674,977 A | 10/1997 | Gariepy | 530/324 |
| 5,679,637 A | 10/1997 | Lappi et al. | 514/2 |
| 5,679,673 A | 10/1997 | Bowen et al. | |
| 5,684,136 A | 11/1997 | Godowski | 530/399 |
| 5,728,802 A | 3/1998 | Barrett et al. | 530/324 |
| 5,759,515 A | 6/1998 | Rhodes et al. | 424/1.69 |
| 5,767,234 A | 6/1998 | Yanofsky et al. | 530/327 |
| 5,770,704 A | 6/1998 | Godowski | 530/402 |
| 5,773,569 A | 6/1998 | Wrighton et al. | 530/300 |
| 5,786,322 A | 7/1998 | Barrett et al. | 514/2 |
| 5,786,331 A | 7/1998 | Barrett et al. | 514/15 |
| 5,789,182 A | 8/1998 | Yayon et al. | 435/721 |
| 5,830,851 A | 11/1998 | Wrighton et al. | 514/2 |
| 5,861,476 A | 1/1999 | Barrett et al. | 530/527 |
| 5,866,113 A | 2/1999 | Hendriks et al. | 424/78.17 |
| 5,869,451 A | 2/1999 | Dower et al. | 514/13 |
| 5,880,096 A | 3/1999 | Barrett et al. | 514/15 |
| 5,902,799 A | 5/1999 | Herrmann et al. | 514/58 |
| 5,932,462 A | 8/1999 | Harris et al. | 435/188 |
| 5,952,474 A | 9/1999 | Kayman et al. | 530/395 |

(Continued)

FOREIGN PATENT DOCUMENTS

| | | |
|---|---|---|
| WO | WO 00/18921 | 4/2000 |
| WO | WO0064481 | 11/2000 |
| WO | WO 02/04015 | 1/2002 |
| WO | WO0210221 | 2/2002 |
| WO | WO 02/19963 | 3/2002 |
| WO | WO 02/20033 | 3/2002 |
| WO | WO-02/062823 | 8/2002 |

OTHER PUBLICATIONS

Peter Carmeliet and Edward M. Conway, "Growing better blood vessels," *Nature Biotechnology* (2001) 19:1019-1020.

Thomas P. Richardson, Martin C. Peters, Alessandra B. Ennett, and David J. Mooney, "Polymeric system for dual growth factor delivery," *Nature Biotechnology* (2001) 19:1029-1034.

Francois Paris, Zvi Fuks, Anthony Kang, Paola Capodieci, Gloria Juan, Desiree Ehleiter, Adriana Haimovitz-Friedman, Carlos Cordon-Cardo, Richard Kolesnick, "Endothelial Apoptosis as the Primary Lesion Initiating Intestinal Radiation Damage in Mice," *Science* (2001) 293:293-297.

(Continued)

*Primary Examiner*—Robert Landsman
*Assistant Examiner*—Ian Dang
(74) *Attorney, Agent, or Firm*—Janeen Vilven; Peacock Myers, P.C.

(57) ABSTRACT

The invention provides synthetic heparin-binding growth factor analogs having at least one peptide chain, and preferably two peptide chains branched from a dipeptide branch moiety composed of two trifunctional amino acid residues, which peptide chain or chains bind a heparin-binding growth factor receptor and are covalently bound to a non-signaling peptide that includes a heparin-binding domain, preferably by a linker, which may be a hydrophobic linker. The synthetic heparin-binding growth factor analogs are useful as pharmaceutical agents, soluble biologics or as surface coatings for medical devices.

12 Claims, 10 Drawing Sheets

U.S. PATENT DOCUMENTS

| | | | |
|---|---|---|---|
| 5,955,588 A | 9/1999 | Tsang et al. | 536/21 |
| 5,965,532 A | 10/1999 | Bachovchin | 514/12 |
| 5,989,866 A | 11/1999 | Deisher et al. | 435/69.4 |
| 5,994,104 A | 11/1999 | Anderson et al. | 435/69.52 |
| 6,001,364 A | 12/1999 | Rose et al. | 424/193.1 |
| 6,011,002 A | 1/2000 | Pastan et al. | 514/2 |
| 6,030,812 A | 2/2000 | Bauer et al. | 435/69.7 |
| 6,051,648 A | 4/2000 | Rhee et al. | 525/54.1 |
| 6,096,798 A | 8/2000 | Luthra et al. | |
| 6,099,562 A | 8/2000 | Ding et al. | |
| 6,120,904 A | 9/2000 | Hostettler et al. | |
| 6,121,236 A | 9/2000 | Ben-Sasson | 514/12 |
| 6,168,784 B1 | 1/2001 | Offord et al. | 424/85.1 |
| 6,174,530 B1 | 1/2001 | Rose et al. | 424/193.1 |
| 6,174,721 B1 | 1/2001 | Innis et al. | 435/320.1 |
| 6,214,795 B1 | 4/2001 | Benjamin et al. | 514/12 |
| 6,217,873 B1 | 4/2001 | Rose et al. | 424/193.1 |
| 6,231,600 B1 | 5/2001 | Zhong | |
| 6,231,892 B1 | 5/2001 | Hubbell et al. | |
| 6,235,716 B1 | 5/2001 | Ben-Sasson | 514/15 |
| 6,248,057 B1 | 6/2001 | Mavity et al. | |
| 6,251,864 B1 | 6/2001 | Dower et al. | 514/13 |
| 6,258,371 B1 | 7/2001 | Koulik et al. | |
| 6,270,788 B1 | 8/2001 | Koulik et al. | |
| 6,284,503 B1 | 9/2001 | Caldwell et al. | 435/181 |
| 6,294,359 B1 | 9/2001 | Fiddes et al. | 435/69.4 |
| 6,306,165 B1 | 10/2001 | Patnaik et al. | |
| 6,309,660 B1 | 10/2001 | Hsu et al. | |
| 6,323,323 B1 | 11/2001 | Sledziewski et al. | 530/387.3 |
| 6,326,468 B1 | 12/2001 | Canne et al. | 530/333 |
| 6,342,591 B1 | 1/2002 | Zamora et al. | 536/21 |
| 6,350,731 B1 | 2/2002 | Jehanli et al. | 514/12 |
| 6,377,349 B1 | 4/2002 | Fercher | 356/450 |
| 6,426,332 B1 | 7/2002 | Rueger et al. | |
| 6,451,653 B2 | 9/2002 | Kochendoerfer et al. | 435/7.1 |
| 6,548,634 B1 | 4/2003 | Ballinger et al. | |
| 6,846,853 B2 | 1/2005 | Shimp | |
| 6,863,899 B2 | 3/2005 | Koblish et al. | |
| 6,949,251 B2 | 9/2005 | Dalal et al. | |
| 7,041,641 B2 | 5/2006 | Rueger et al. | |
| 7,166,574 B2 | 1/2007 | Pena et al. | |
| 7,414,028 B1 | 8/2008 | Zamora et al. | |
| 7,468,210 B1 | 12/2008 | Zamora | |
| 7,482,427 B2 | 1/2009 | Pena et al. | |
| 7,528,105 B1 | 5/2009 | Pena et al. | |
| 2001/0014662 A1 | 8/2001 | Rueger et al. | |
| 2003/0224996 A1 | 12/2003 | Opperman et al. | |
| 2004/0038348 A1 | 2/2004 | Pena et al. | |
| 2004/0151764 A1 | 8/2004 | Zamora | |
| 2005/0196425 A1 | 9/2005 | Zamora | |
| 2005/0222394 A1 | 10/2005 | Zamora et al. | |
| 2006/0024347 A1 | 2/2006 | Zamora et al. | |
| 2006/0199764 A1 | 9/2006 | Zamora et al. | |
| 2006/0205652 A1 | 9/2006 | Zamora et al. | |
| 2008/0063622 A1 | 3/2008 | Zamora et al. | |
| 2008/0160169 A1 | 7/2008 | Zamora et al. | |
| 2008/0166392 A1 | 7/2008 | Zamora et al. | |
| 2008/0227696 A1 | 9/2008 | Takahashi et al. | |
| 2009/0111743 A1 | 4/2009 | Takahashi | |
| 2009/0143566 A1 | 6/2009 | Zamora et al. | |

OTHER PUBLICATIONS

Luca Pellegrini, "Role of heparan sulfate in fibroblast growth factor signalling: a structural view," *Structural Biology* (2001) 11:629-634.

Takumi Takizawa, Makoto Yanagisawa, Wataru Ochiai, Kiyoshi Yasukawa, Takahiko Ishiguro, Kinichi Nakashima, Tetsuya Taga, "Directly Linked Soluble IL-6 Receptor-IL-6 Fusion Protein Induces Astrocyte Differentiation From Neuroepithelial Cells Via Activation of STAT3," *Cytokine* (2001) 13:272-279.

Atsuko Yoneda, Masahiro Asada, Yuko Oda, Masashi Suzuki, and Toru Imamura, "Engineering of an FGF-proteoglycan fusion protein with heparin-independent, mitogenic activity," *Nature Biotechnology* (2000) 18:641-644.

Anaera Verrecchio, Markus W. Germann, Barbara P. Schick, Brian Kung, Thomas Twardowski, and James D. San Antonio, Design of Peptides with High Affinities for Heparin and Endothelial Cell Proteoglycans, *The Journal of Biological Chemistry* (2000) 275: 7701-7707.

Marcus D. Ballinger, Venkatakrishna Shyamala, Louise D. Forrest, Maja Deuter-Reinhard, Laura V. Doyle, Jian-xin Wang, Lootsee Panganiban-Lustan, Jennifer R. Stratton, Gerald Apell, Jill A. Winter, Michael V. Doyle, Steven Rosenberg, and W. Michael Kavanaugh, "Semirational design of a potent, artificial agonist of fibroblast growth factor receptors," *Nature Biotechnology* (1999) 17:1199-1204.

Maemaunah Hasan, Saloua Najjam, Myrtle Y. Gordon, Roslyn V. Gibbs, and Christopher C. Rider, "IL-12 is a Heparin-Binding Cytokine," *The Journal of Immunology* (1999) 162: 1064-1070.

R. Sood, A. Talwar-Trikha, SR Chakrabarti and G. Nucifor, "MDS1/ EVI1 enhances TGF-B1 signaling and strengthens its growth-inhibitory effect, but the leukemia-associated fusion protein AML1/MDS1/ CVI1, product of the t(3:21), abrogates growth-inhibition in response to TGF-B1," *Leukemia* (1999) 13: 348-357.

Jose A. Andrades, Bo Han, Jose Becerra, Nino Sorgente, Frederick L. Hall, and Marcel E. Nimni, "A Recombinant Human TGF-B1 Fusion Protein with Collagen-Binding Domain Promotes Migration, Growth, and Differentiation of Bone Marow Mesenchymal Cells," *Experimental Cell Research* (1999) 250:485-498.

Marco Rusnati, Elena Tanghetti, Patrizia Dell'Era, Anna Gualandris, and Marco Presta, "avB3 Integrin Mediates the Cell-adhesive Capacity and Biological Activity of Basic Fibroblast Growth Factor (FGF-2) in Cultured Endothelial Cells," *Molecular Biology of the Cell* (1997) 8:2449-2461.

Jasodhara Ray, Andrew Baird, and Fred H. Gage, "A 10-amino acid sequence of fibroblast growth factor 2 is sufficient for its mitogenic activity on neural progenitor cells," *Proc. Natl. Acad. Sci. USA* (1997) 94:7047-7052.

Arne Ostman, Maria Andersson, Ulf Hellman, and Carl-Henrik Heldin, "Identification of Three Amino Acids in the Platelet-derived Growth Factor (PDGF) B-chain That Are Important for Binding to the PDGF B-Receptor" *The Journal of Biological Chemistry*, vol. 266, No. 16, Issue of Jun. 5, pp. 10073-10077, 1991.

David M. Brennand, Ulla Dennehy, Vincent Ellis, Michael F. Scully, Poonam Tripathi, Vijay V. Kakkar, Geeta Patel, "Identification of a cyclic peptide inhibitor of platelet-derived growth factor-BB receptor-binding and mitogen-induced DNA synthesis in human fibroblasts," *FEBS Letters* 413 (1997) 70-74.

Ahmed, Asif; Dunk, Caroline; Kniss, Douglas; Wilkes, Mark, "Role of VEGF Receptor-1 (Fit-1) in Mediating Calcium-Dependent Nitric Oxide Release and Limiting DNA Synthesis in Human Trophoblast Cells," *Lab Invest*, vol. 76(6) Jun. 1997.779-791.

Philip E. Dawson and Stephen B. H. Kent, "Synthesis of Native Proteins by Chemical Ligation," *Annu. Rev. Biochem.* 2000, 69:923-60.

Roselyne Binetruy-Tournaire, Caroline Demangel, Bernard Malavaud, Roger Vassy, Sylvie Rouyre, Michael Kraemer, Jean Plouet, Claude Derbin, Gerard Perret and Jean Claude Mazie, "Identification of a peptide blocking vascular endothelial growth factor (VEGF)-mediated angiogenesis," *The EMBO Journal* vol. 19 No. 7 pp. 1525-1533, 2000.

Khee Dong Eom, Zhenwei Miao, Jin-Long Yang, and James P. Tam, "Tandem Ligation of Multipartite Peptides with Cell-Permeable Activity," *J. Am. Chem. Soc.* 2003, 125, 73-83.

Gerd G. Kochendoerfer, Shiah-Yun Chen, Geng Mao, Sonya Cressman, Stacey Traviglia, Haiyan Shao, Christie L. Hunter, Donald W. Low, E. Neil Cagle, Maia Carnevali, Vincent Gueriguian, Peter J. Keoch, Heather Porter, Stepehn M. Stratton, M. Con Wiedeke, Jill Wilken, Jie Tang, Jay J. Levy, Les P. Miranda, Milan M. Crnogorac, Suresh Kalbag, Paolo Botti, Janice Schindler-Horvat, Laura Savatski, John W. Adamson, Ada Kung, Stepehn B. H. Kent, James a Bradburne, "Design and Chemical Synthesis of Homogeneous Polymer-Modified Erythropoiesis Protein," *Science*, Feb. 7, 2003, vol. 299.

Michael M. Dikov, Martha B. Reich, Lydia Dworkin, James W. Thomas, and Geraldine G. Miller, A Functional Fibroblast Growth Factor-1 Immunoglobulin Fusion Protein, *The Journal of Biological Chemistry*, vol. 273, No. 25, Ussue of Jun. 19, pp. 15811-15817, 1998.

Ulla Engstrom, Ake Engstrom, Agneta Ernlund, Bengt Westermark, and Carl-Henrik Heldin, "Identification of a Peptide Antagonist for Platelet-derived Growth Factor," *The Journal of Biological Chemistry*, vol. 267, No. 23, Issue of Aug. 15, pp. 16581-16587, 1992.

David E. Hoke, Daniel Carson, and Magnus Hook, "A heparin binding synthetic peptide from human HIP/RPL29 fails to specifically differentiate between anticoagulantly active and inactive species of heparin," *Journal of Negative Results* in BioMedicine 2003, 2:1.

Gay, Cyril G. and Winkles, Jeffrey A.; Interleukin 1 regulates heparin-binding growth facto 2 gene expression in vascular smooth muscle cells; Proc. Natl. Acad. Sci. USA, Vol. 88, pp. 296-300, Jan. 1991 Cell Biology.

Bork, Peer et al., "Go Hunting in Sequence Databases But Watch Out For Traps", *TIG* Oct. 1996, 425-427.

Bork, Peer et al., "Powers and Pitfalls in Sequence Analysis: the 70% Hurdle", *Genome Research* 2000, 398-400.

Brenner, Steve et al., "Errors in Genome Annotation", *Trends in Genetics* Apr. 1999, 132-133.

Doerks, Tobias et al., "Protein annotation: detective work for function prediction", *Trends in Genetics* Jun. 1998, 248-250.

Ngo, Thomas et al., "Computational Complexity; Protein Structure Prediction, and the Levinthal Paradox", *The Protein Foling Problem and Terminary Structure Prediction* 1994.

Skolnick, Jeffrey et al., "From genes to protein structure and function: novel applications of computational approaches in the genomic era", *TIBTECH* Jan. 2000, 34-39.

Smith, Temple F. et al., "The challenges of genome sequence annotation of "The devil is in the details"", *Nature Biotechnology*, vol. 15 Nov. 1997, 1222-1223.

Wells, James A. et al., "Additivity of Mutational Effects in Proteins", *American Chemical Society*, vol. 29, No. 37 Sep. 18, 1990, 8509-8516.

Baird, Andrew et al., "Receptor- and heparin-binding domains of basic fibroblast growth factor", Proc. Natl. Acad. Sci., vol. 85 Apr. 1988, 2324-2328.

Feeley, Brian et al., "Influence of BMP's on the Formation of Osteoblastic Lesions in Metastatic Prostate Cancer", *Journal of Bone and Mineral Research*, vol. 20 No. 12 2005, 2189-2199.

Healy, Kevin et al., "Designing biomaterials to direct biological responses", Ann N Y Acad Sci. 875 1999, 24-35.

Kirsch, Thomas et al., "BMP-2 Antagonists Emerge from Alterations in the Low-Affinity Binding Epitope for Receptor BMPR-II", *EMBO Journal*, vol. 19, No. 13 2000, 3314-3324.

Kloen, P. et al., "BMP signaling components are expressed in human fracture callus", *Bone 33* 2003, 362-371.

Konishi, Sadahiko et al., "Hydroxyapatite Granule Graft Combined with Recombinant Human bone Morphogenetic Protein-2 for Solid Lumbar Fusion", *Journal of Spinal Disorders & Technisues* vol. 15 No. 3 2002, 237-244.

Laredo, James et at., "Silyl-heparin bonding improves the patency and in vivo thrombroesistance of carbon-coated polytetrafluoroethylene vascular grafts", *The Midwestern Vascular Surgical Society* Sep. 2003, 1-7.

Lu, Xinjie et al., "Preferential antagonism of the interactions of the integrin alpha IIb beta 3 with immobilized glycoprotein ligans by snake-venom RGD (Arg-Gly-Asp) proteins", *Biochem J 304* 1994, 929-936.

Minamide, Akihito et al., "Evaluation of Carriers of Bone Morphogenetic Protein for Spinal Fusion", *Spine* vol. 26, No. 8 2001, 933-939.

Murnaghan, Mark et al., "Time for treating bone fracture using rhBMP-2: A randomised placebo controlled mouse fracture trial", *Journal of Orthopaedic Research 23* 2005, 625-631.

Niikura, T. et al., "Gloval Gene Profiling in Experimental Fracture Nonunions Reveals a Down Regulation of BMP Gene Expression", *52nd Annual Meeting of The Orthopaedic Research Society*, Paper No. 1673 2006.

Saito, Atsuhiro et al., "Activation of osteo-progenitor cells by a novel synthetic peptide derived from the bone morphogenetic protein-2 knuckle epitope", *Biochimica et Bioptysica Acta 1651* 2003, 60-67.

Saito, Atsuhiro et al., "Prolonged ectopic calcification induced by BMP-2-derived synthetic peptide", www.interscience.wiley.com 2004, 1-7.

Seol, Yang-Jo et al., "Enhanced osteogenic promotion around dental implants with synthetic binding motif mimicking bone morphogenetic protein (BMP)-2", *Journal of Biomedical Materials Research Part A*; www.interscience.wiley.com 2005, 1-8.

Shen, Wei-Chiang et al., "Poly(l-lysine) has different membrane transport and drug-carrier properties when complexed with heparin", *Proc Natl Acad Sci USA* Dec. 1981, 7589-93.

Smith, Temple F. et al., "The challenges of genome sequence annotation of "The devil is in the details"", *Nature Biotechnology*, vol. 15 Nov. 1997, 1222-1223.

Tanaka, H. et al., "Involvement of bone morphogenic protein-2 (BMP-2) in the pathological ossification process of the spinal ligament", *Rheumatology 2001*; 40 May 9, 2001, 1163-1168.

Tong, Yen et al., "Peptide surface modification of poly(tetrafluoroethylene-co-hexafluoropropylene) enhances its interaction with central nervous system nuerons", *J Biomed Mater Res 42* 1998, 85-95.

Tung, Ching-Hsuan et al., "Novel branching membrane translocational peptide as gene delivery vector", *Bioorg Med Chem* 10(11) 2002, 3609-3614.

Varkey, Mathew et al., "Growth factor delivery for bone tissue repair: an update", *Expert Opin. Drug Deliver.* (2004) 1 (1) 2004, 19-34.

Wells, James A., "Additivity of Mutational Effects in Proteins", *American Chemical Society*, vol. 29, No. 37 Sep. 18, 1990, 8509-5816.

Yano, Akira et al., "RGD motif enhances immunogenicity and adjuvanicity of peptide antigens following intranasal immunization", *Vaccine* 22(2) 2003, 237-243.

Zamora, Paul O. et al., "Local Delivery of Basic Fibroblast Growth Factor (bFGF) Using Adsorbed Silyl-heparin, Benzyl-bis(dinnethylsilylmethyl)oxycarbamoyl-heparin", *Bioconjugate Chem. 2002* Aug. 20, 2002, 920-926.

NH₂-K-K-Hex-Hex-Hex-RKRKLERIAR-amide

```
    |   |   _____/  _____/
    Y   Y  ⎫                     Heparin
    R   R  ⎬   C18 spacer        Binding
    S   S  ⎭                     Domain
    R   R  ⎫
    K   K  ⎪
    Y   Y  ⎪
    S   S  ⎪
    S   S  ⎪   Receptor
    W   W  ⎬   Binding
    Y   Y  ⎪   Domain
    V   V  ⎪
    A   A  ⎪
    L   L  ⎪
    K   K  ⎪
    R   R  ⎭
    |   |
   NH₂ NH₂
```

FIG. 2

SYNTHETIC HEPARIN-BINDING FACTOR ANALOGS

CROSS-REFERENCE TO RELATED APPLICATIONS

This application is a continuation-in-part application of and claims priority to U.S. patent application Ser. No. 10/224, 268, entitled *Synthetic Heparin-Binding Growth Factor Analogs*, filed on Aug. 20, 2002, which issued as U.S. Pat. No. 7,166,574 and the specification thereof is incorporated herein by reference.

STATEMENT REGARDING FEDERALLY SPONSORED RESEARCH OR DEVELOPMENT

This invention was made with United States Government support under contract number DE-AC02-98CH10886, awarded by the U.S. Department of Energy. The United States Government has certain rights in the invention.

FIELD OF THE INVENTION

The invention relates to the field of synthetic peptides and analogs of heparin-binding growth factors, particularly analogs further having a non-growth factor heparin-binding region and optionally a linker, which linker may be hydrophobic. The invention further relates to the clinical uses of such analogs as soluble drugs and as coatings for medical devices.

BACKGROUND

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

The heparin-binding growth factors (HBGFs) constitute a large class of growth factors that includes the 23 fibroblast growth factors identified to date (FGFs 1-23), HBBM (heparin-binding brain mitogen), HB-GAF (heparin-binding growth associated factor), HB-EGF (heparin-binding EGF-like factor) HB-GAM (heparin-binding growth associated molecule), TGF-α (transforming growth factor-α), TGF-βs (transforming growth factor-βs), PDGF (platelet-derived growth factor), EGF (epidermal growth factor), VEGF (vascular endothelial growth factor), IGF-1 (insulin-like growth factor-1), IGF-2 (insulin-like growth factor-2), HGF (hepatocyte growth factor), IL-1 (interleukin-1), IL-2 (interleukin-2), IFN-α (interferon-α), IFN-γ (interferon-γ), TNF-α (tumor necrosis factor-α), SDGF (Schwannoma-derived growth factor) and the many other growth factors, cytokines, lymphokines and chemokines that have an affinity for heparin.

Peptides from natural HBGFs that bind heparin-binding growth factor receptors have been identified. See for example Ray et al., Proc. Natl. Acad. Sci. USA 94:7047-7052 (1997). These authors demonstrated that two amino acid sequences from FGF-2 are sufficient to block the mitogenic activity of FGF-2 on neural progenitor cells. The first peptide is a ten amino acid sequence, from amino acids 65-74, the second peptide extends from amino acids 115-129.

In an alternative approach, an artificial peptide that binds a heparin-binding growth factor receptor was identified by a phage display method. Ballinger et al., Nature BioTechnology 17:1199-1204 (1999) used this technique to isolate a 28 amino acid peptide called C19, binds FGF-2 receptors, but by itself fails to stimulate biological activity. The peptide has no amino acid sequence identity with any known FGF.

HBGFs useful in prevention or therapy of a wide range of diseases and disorders may be purified from natural sources or produced by recombinant DNA methods, however, such preparations are expensive and generally difficult to prepare.

Some efforts have been made to generate heparin-binding growth factor analogs. For example, natural PDGF occurs as an A chain and a B chain arranged in head-to-head (AA or BB) homodimers, or (AB or BA) heterodimers. Thus, U.S. Pat. No. 6,350,731 to Jehanli et al. discloses PDGF analogs in which two synthetic PDGF receptor-binding domains are covalently linked through a polyglycine or an N-(4-carboxy-cyclohexylmethyl)-maleimide (SMCC) chain to mimic the natural active polypeptide dimer.

U.S. Pat. No. 6,235,716 to Ben-Sasson discloses analogs of angiogenic factors. The analogs are branched multivalent ligands that include two or more angiogenic homology regions connected by a multilinker backbone.

U.S. Pat. No. 5,770,704 (the '704 patent) to Godowski discloses conjugates for activating receptor tyrosine kinases, cytokine receptors and members of the nerve growth factor receptor superfamily. The conjugates include at least two ligands capable of binding to the cognate receptor, so that the binding of the respective ligands induces oligomerization of these receptors. The ligands disclosed in the '704 patent are linked by covalent attachment to various nonproteinaceous polymers, particularly hydrophilic polymers, such as polyvinylalcohol and polyvinylpyrrolidone, and the polyvinylalkene ethers, including polyethylene glycol and polypropylene glycol. The ligands include hepatocyte growth factor (HGF) peptide variants that each bind HGF receptor, thereby causing receptor dimerization and activation of the biological activity of the HGF receptor dimer.

U.S. Pat. No. 6,284,503 (the '503 patent) to Caldwell et al. discloses a composition and method for regulating the adhesion of cells and biomolecules to hydrophobic surfaces and hydrophobic coated surfaces for cell adhesion, cell growth, cell sorting and biological assays. The composition is a biomolecule conjugated to a reactive end group activated polymer. The end group activated polymer includes a block copolymer surfactant backbone and an activation or reactive group. The block copolymer may be any surfactant having a hydrophobic region capable of adsorbing onto a hydrophobic surface, and a hydrophilic region which extends away from the surface when the hydrophobic region is adsorbed onto the hydrophobic surface. The '503 patent discloses that the biomolecules that may be conjugated to the end group activated polymer include natural or recombinant growth factors, such as PDGF, EGF, TGFα, TGFβ, NGF, IGF-I, IGF-II, GH and GHRF, as well as multi-CSF(II-3), GM-CSF, G-CSF, and M-CSF.

Other workers have described compositions that include homologs and analogs of fibroblast growth factors (FGFs). See for example U.S. Pat. No. 5,679,673 to Lappi and Baird; U.S. Pat. No. 5,989,866 to Deisher et al. and U.S. Pat. No. 6,294,359 to Fiddes et al. These disclosures relate to FGF homologs or analogs that are either conjugated to a toxic moiety and are targeted to the FGF receptor-bearing cells; or are homologs or analogs that modulate the biological pathways through the signal transduced by the FGF receptor upon binding by the FGF homolog or analog.

A series of patent applications to Kochendoerfer et al. disclose polymer-modified proteins, including synthetic chemokines and erythropoiesis stimulating proteins. See, for example, International Publications WO 02/04105, WO 02/19963 and WO 02/20033. These include chemically ligated peptide segments of a polypeptide chain of a synthetic erythropoiesis protein, such that a polypeptide chain results, with a water soluble polymer attached at one or more glycosylation sites on the protein. These applications also disclose synthetic chemokines, which are also polymer modified, and are asserted to be antagonists. However, heparin-binding domains are not disclosed. Other erythropoietin mimetics are known, such as those disclosed in U.S. Pat. Nos. 5,773,569 and 5,830,851 to Wrighton et al.

International Publication WO 00/18921 to Ballinger and Kavanaugh discloses a composition consisting of fusion proteins having FGF receptor affinity linked to an "oligomerization domain", either directly or through a linking group. The oligomerization domain ranges in length from about 20 to 300 residues, and includes constructs such as transcription factors, Fc portions of IgG, leucine zippers and the like. The oligomerization domains disclosed are homodimeric domains, wherein a single FGF receptor affinity fusion protein is linked to a single domain, such as a leucine zipper, which in turn is linked to a similar molecule by means of cysteine residues at both the amino and carboxy termini of the leucine zippers, such that two parallel leucine zippers, each with a single FGF receptor affinity fusion protein, are cross-linked by means of disulfide bonds. It is also disclosed that fusion proteins may include a heparin binding domain, such as the use of jun as a multimerization domain, which is asserted to be a heparin binding domain. Thus the compositions disclosed by Ballinger and Kavanaugh are all composed of a single receptor-binding sequence covalently attached to an oligomerization domain, whereby two or more similar oligomerization domains, each with a single receptor-binding sequence, are conjoined by means of either an association provided by the oligomerization domain, or alternatively, are chemically cross-linked to provide for the covalent bonding of the individual components.

The above described homologs, analogs, conjugates or ligands each include a receptor-binding domain. However, none of the disclosed compositions further include both a linker, providing for the linking of two receptor-binding domains to a dipeptide sequence, and further providing a single non-signaling peptide containing a heparin-binding domain. Moreover, none of these or other known heparin-binding growth factor analogs provide the advantages described herein below. There is still a need for new peptide analogs of HBGFs, particularly for those that function as agonists. In particular, there is still a need for cost-effective synthetic peptide agonists of heparin-binding growth factor receptors, particularly synthetic heparin-binding growth factor agonists useful for coating medical devices and as soluble biologics.

SUMMARY OF THE INVENTION

In one embodiment, the invention provides a HBGF analog of formula I:

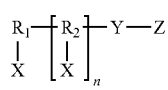

wherein each X is a peptide chain that (i) has a minimum of three amino acid residues, (ii) has a maximum of about fifty amino acid residues, and (iii) binds a heparin-binding growth factor receptor (HBGFR); $R_1$ is an amino acid residue, wherein X is covalently bonded through the N-terminus of $R_1$ or through a side chain of $R_1$; $R_2$ is a trifunctional alpha amino acid residue, wherein X is covalently bonded through a side chain of $R_2$; Y is a linker comprising a chain from 0 to about 50 atoms covalently bonded to $R_1$ and Z when n=0, or to $R_2$ and Z when n=1; Z is a non-signaling peptide chain that comprises a heparin binding domain, comprising an amino acid sequence that comprises (i) a minimum of one heparin binding motif, (ii) a maximum of about ten heparin binding motifs, and (iii) a maximum of about thirty amino acids; and, n is 0 or 1, wherein when n=1 the peptide chains X are identical.

In the HBGF analog of formula I, Y can further include a linker that (i) is hydrophobic, (ii) comprises a chain of a minimum of about 9 and a maximum of about 50 atoms, and (iii) is not found in the natural ligand of the HBGFR which X binds. In one embodiment of formula I, $R_1$ is a trifunctional amino acid residue, wherein X is covalently bonded through a side chain of $R_1$.

In one embodiment of formula I, the HBGF analog of formula I is characterized in that it has an avidity for heparin such that the it binds heparin in 0.15 M NaCl, but is eluted by 1 M NaCl.

In another embodiment, the invention provides an HBGF analog of formula II:

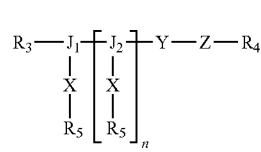

wherein $R_3$ and $R_5$ are each independently $NH_2$, an acyl group with a linear or branched $C_1$ to $C_{17}$ alkyl, aryl, heteroaryl, alkene, alkenyl or aralkyl chain including a N-terminus $NH_2$, $NH_3^+$, or NH group or a corresponding acylated derivative, or is an amino acid, a dipeptide or a tripeptide, with an N-terminus $NH_2$, $NH_3^+$, NH group or a corresponding acylated derivative; $R_4$ is —OH, $NH_2$, NH—$R_6$, or is an amino acid, a dipeptide or a tripeptide with a C-terminus —OH, $NH_2$, or NH—$R_6$; $R_6$ is an aliphatic $C_1$ to $C_{17}$ chain; each X is a peptide chain that (i) has a minimum of three amino acid residues, (ii) has a maximum of about fifty amino acid residues, and (iii) binds a HBGFR; $J_1$ and $J_2$ are each independently a trifunctional alpha amino acid residue, wherein each X is covalently bonded through a side chain of $J_1$ or $J_2$; Y is a linker comprising a chain from 0 to about 50 atoms covalently bonded to $J_1$ and Z when n=0, or to $J_2$ and Z when n=1; Z is a non-signaling peptide that comprises a heparin binding domain, comprising an amino acid sequence that comprises (i) a minimum of one heparin binding motif, (ii) a maximum of about ten heparin binding motifs, and (iii) a maximum of about thirty amino acids; and, n is 0 or 1, wherein when n=1 the synthetic peptide chains X are identical.

In the HGBF analog of formula II, Y can further include a linker that (i) hydrophobic, (ii) comprises a chain of a minimum of about 9 and a maximum of about 50 atoms, and (iii) is not found in the natural ligand of the HBGFR which X binds.

In one embodiment, the HBGF analog of formula II is characterized in that it has an avidity for heparin such that it binds heparin in 0.15 M NaCl, but is eluted by 1 M NaCl.

The HBGF analog of formula II can further be characterized in that binding of it to the HBGFR initiates a signal by the HBGFR, or alternatively in that it blocks signaling by the HBGFR.

In one embodiment of the HBGF analog of formula II, $J_1$ and, if n=1, $J_2$, is a diamine amino acid residue. Such diamine amino acid residue may be a 2,3 diamino propionyl amino acid residue, a lysyl residue or an ornithinyl residue. In an alternative embodiment of the HBGF analog of formula II, the side chain of $J_1$ and, if n=1, $J_2$, includes a reactive carboxyl group.

In one embodiment of the HBGF analog of formula II, the covalent bond between X and $J_1$ or, if n=1, $J_2$, comprises an amide, disulfide, thioether, Schiff base, reduced Schiff base, imide, secondary amine, carbonyl, urea, hydrazone or oxime bond. In a preferred embodiment, the bond is an amide bond.

The HBGF analog of formula II thus includes a HBGF analog of formula III:

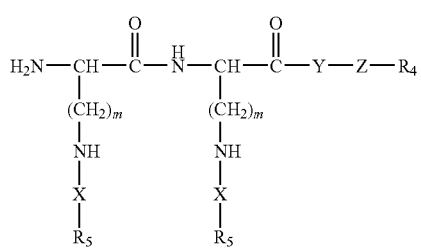

III wherein m is from 1 to about 10.

The HBGF analog of formula III thus further includes a HBGF analog of formula IV:

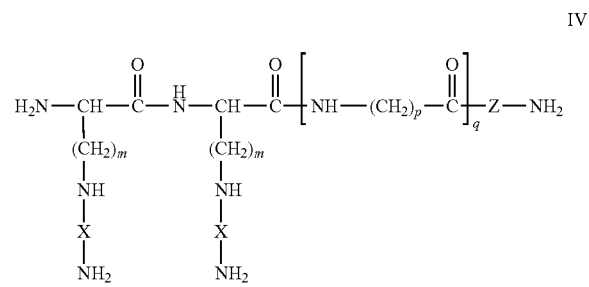

IV wherein p is from 1 to about 10 and q is from 1 to about 20. In one particularly preferred embodiment, p is 5 and q is three.

In one embodiment, in the HBGF analog of any of formula I or II where n=1, or of formula III or IV, the peptide chains X are cross-linked or cyclized. Such cross-linking or cyclization may be through a covalent bond, including at least one disulfide, peptide, amide or thioether bond.

In another embodiment, in the HBGF analog of any of formula I, II or III, Y includes between one and about thirty-three ethylene glycol (oxyethylene) units. Alternatively, Y may include a branched or unbranched, saturated or unsaturated alkyl chain of between one and about twenty carbon atoms. In a particularly preferred embodiment, Y is $[NH_2-(CH_2)_pCO]_q$ wherein p is from 1 to about 10 and q is from 1 to about 20. In another embodiment, Y includes a peptide sequence, and in a preferred embodiment, with from one to about 16 Gly residues.

In another embodiment of the HBGF analog of any of formula I, II, III or IV, each heparin binding motif of Z is BxBB, or BBBxxB, wherein each B independently represents lysine, arginine, ornithine, or histidine, and x represents a naturally occurring amino acid. In a preferred embodiment, Z includes at least two heparin-binding motifs, more preferably at least five heparin-binding motifs.

The present invention further includes a pharmaceutical composition including the HBGF analog of any of formula I, II, III or IV, or a pharmaceutically acceptable salt thereof, and a pharmaceutical carrier.

The present invention yet further provides a method for treating a mammal that has been exposed to a harmful dose of radiation or a chemotherapeutic agent, the method comprising administering to the mammal an effective dose of a HBGF analog of any of formula I, II, III or IV. Particularly preferred are HBGF wherein X binds an FGF HBGFR, and more preferably an FGF-7 receptor. The method includes administering to the mammal an effective dose of the synthetic heparin-binding growth factor analog to ameliorate the harmful effects of the radiation or chemotherapeutic agent, which may include mucositis, G.I. syndrome, or radionecrosis.

The present invention also provides a method for delivering an active peptide to a mammal, particularly a human. The method includes providing a medical device coated on the surface thereof via non-covalent bonds with a HBGF analog of any of formula I, II, III or IV and placing the medical device onto a surface of, or implanting the medical device into, the mammal.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE FIGURES

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 2 depicts the sequence of synthetic peptide analog F2A4 wherein the heparin binding domain is SEQ ID NO:2, the receptor binding domain is SEQ ID NO:6 and the C18 spacer is Hex which is an abbreviation for aminohexanoic acid.

DETAILED DESCRIPTION OF THE INVENTION

Figure 1:
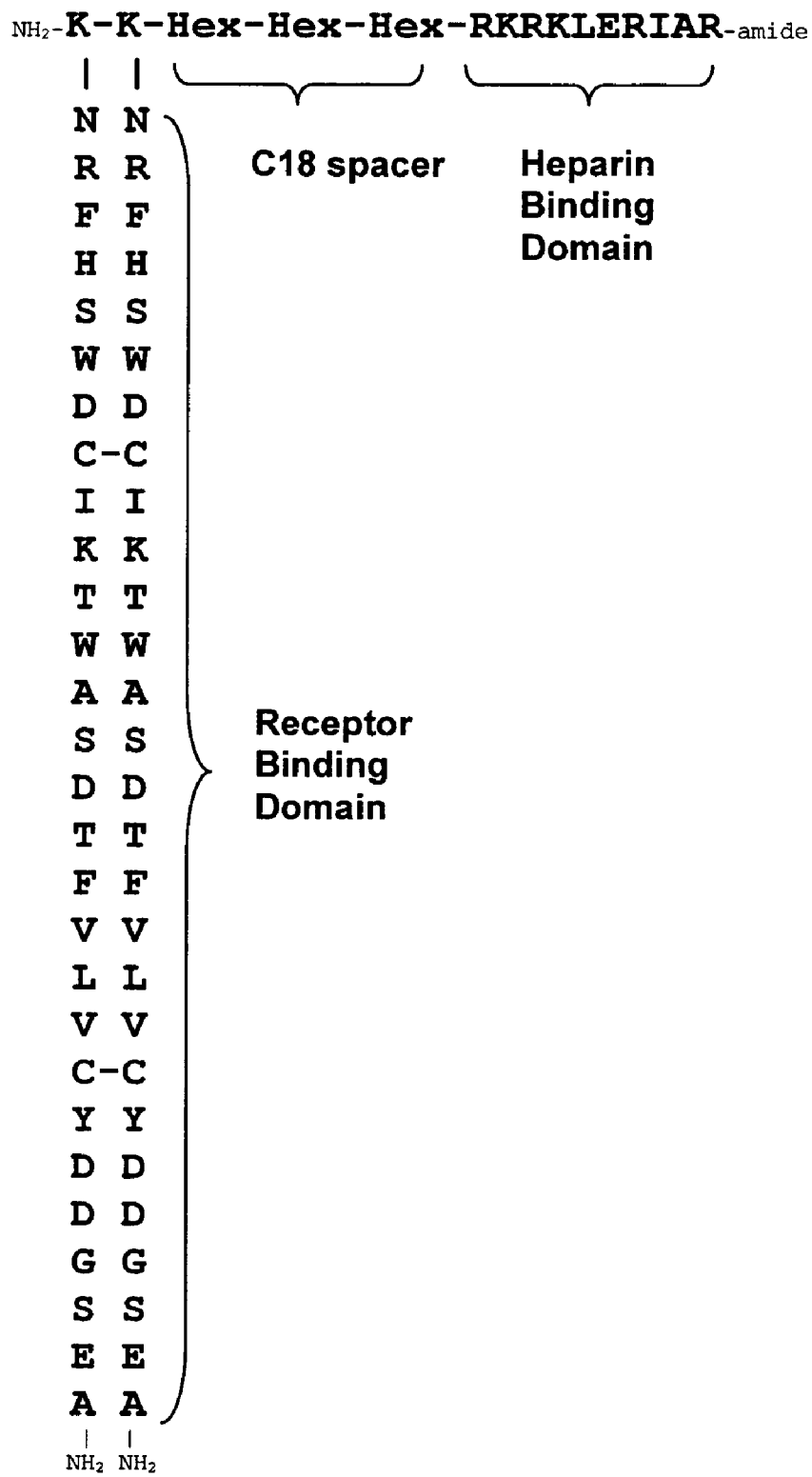
FIG. 1 depicts the sequence of synthetic peptide analog F2A3 wherein the heparin binding domain is SEQ ID NO:2, the receptor binding domain is SEQ ID NO:7 and the C18 spacer is Hex which is an abbreviation for aminohexanoic acid.

Each synthetic HBGF analog of the invention is an analog of a particular HBGF that binds to one or more of the receptors bound by the particular HBGF. The synthetic HBGF analog may be an analog of a hormone, a cytokine, a lymphokine, a chemokine or an interleukin.

In one aspect the synthetic HBGF analog of the present invention is a molecule of any one of formula I, II, III or IV. HBGFs include any growth factor that binds selectively to heparin. For example, the HBGF can be any of the known FGFs (FGF-1 to FGF-23), HBBM (heparin-binding brain mitogen), HB-GAF (heparin-binding growth associated factor), HB-EGF (heparin-binding EGF-like factor) HB-GAM (heparin-binding growth associated molecule, also known as pleiotrophin, PTN, HARP), TGF-α (transforming growth factor-α), TGF-βs (transforming growth factor-βs), VEGF (vascular endothelial growth factor), EGF (epidermal growth factor), IGF-1 (insulin-like growth factor-1), IGF-2 (insulin-like growth factor-2), PDGF (platelet derived growth factor), RANTES, SDF-1, secreted frizzled-related protein-1 (SFRP-1), small inducible cytokine A3 (SCYA3), inducible cytokine subfamily A member 20 (SCYA20), inducible cytokine subfamily B member 14 (SCYB14), inducible cytokine subfamily D member 1 (SCYD1), stromal cell-derived factor-1 (SDF-1), thrombospondins 1, 2, 3 and 4 (THBS1-4), platelet factor 4 (PF4), lens epithelium-derived growth factor (LEDGF), midikine (MK), macrophage inflammatory protein (MIP-1), moesin (MSN), hepatocyte growth factor (HGF, also called SF), placental growth factor, IL-1 (interleukin-1), IL-2 (interleukin-2), IL-3 (interleukin-3), IL-6 (interleukin-6), IL-7 (interleukin-7), IL-10 (interleukin-10), IL-12 (interleukin-12), IFN-α (interferon-α), IFN-γ(interferon-γ), TNF-α (tumor necrosis factor-α), SDGF (Schwannoma-derived growth factor), nerve growth factor, neurite growth-promoting factor 2 (NEGF2), neurotrophin, BMP-2 (bone morphogenic protein 2), OP-1 (osteogenic protein 1, also called BMP-7), keratinocyte growth factor (KGF), interferon-γ inducible protein-20, RANTES, and HIV-tat-transactivating factor, amphiregulin (AREG), angio-associated migratory cell protein (AAMP), angiostatin, betacellulin (BTC), connective tissue growth factor (CTGF), cysteine-rich angiogenic inducer 61 (CYCR61), endostatin, fractalkine/neuroactin, or glial derived neurotrophic factor (GDNF), GRO2, hepatoma-derived growth factor (HDGF), granulocyte-macrophage colony stimulating factor (GMCSF), and the many growth factors, cytokines, interleukins and chemokines that have an affinity for heparin.

The amino acid sequences of many of these and other HBGFs are available from the National Library of Medicine Protein Database at the world wide web address ncbi.nlm.nih.gov/entrez. These HBGF amino acid sequences on the foregoing internet site are hereby incorporated by reference. The use of synthetic HBGF analogs incorporating the amino acid sequences of the receptor binding domains from these and other HBGFs is specifically contemplated in the present invention.

In particular embodiments of the present invention, the synthetic HBGF analog of the present invention consists essentially of the molecule of any one of formula I, II, III or IV, i.e. the molecule of any one of formula I, II, III or IV is the major active component in the synthetic HBGF analog composition.

In other particular embodiments, the synthetic HBGF analog of the present invention consists entirely of the molecule of any one of formula I, II, III or IV, i.e. the molecule of any one of formula I, II, III or IV is the only component in the synthetic HBGF analog composition.

The Heparin-binding Growth Factors of Formulas I to IV

The regions X and Z of the synthetic HBGF analogs of formulas I to IV include amino acid residues, and optionally the region Y includes amino acid residues. An amino acid residue is defined as —NHRCO—, where R can be hydrogen or any organic group. The amino acids can be D-amino acids or L-amino acids. Additionally, the amino acids can be α-amino acids, β-amino acids, γ-amino acids, or δ-amino acids and so on, depending on the length of the carbon chain of the amino acid.

The amino acids of the X, Y and Z component regions of the synthetic HBGF analogs of the invention can include any of the twenty amino acids found naturally in proteins, i.e. alanine (ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine, (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

Furthermore, the amino acids of the X, Y and Z component regions of the synthetic HBGF analogs of the invention can include any of the naturally occurring amino acids not found naturally in proteins, e.g. β-alanine, betaine (N,N,N-trimethylglycine), homoserine, homocysteine, γ-amino butyric acid, ornithine, and citrulline.

Additionally, the amino acids of the X, Y and Z component regions of the synthetic HBGF analogs of the invention can include any of the non-biological amino acids, i.e. those not normally found in living systems, such as for instance, a straight chain amino-carboxylic acid not found in nature. Examples of straight chain amino-carboxylic acids not found in nature include 6-aminohexanoic acid, 7-aminoheptanoic acid, 9-aminononanoic acid and the like.

In formula I or II when n is 0, the molecule of the present invention includes a single X region. When n is 0, the molecules of formula I can be linear (X is covalently bound to $R_1$ through the N-terminus of $R_1$, as through a peptide bond), such that the molecule is a linear chain, or branched (X is covalently bound to $R_1$ through the side chain of $R_1$, as through an amide bond where $R_1$ is a diamine amino acid residue). When n is 1 in formula I or II, the molecule includes two X regions that are identical in amino acid sequence. Thus where n is 1, the molecule is a branched chain that may also be constrained by cross-links between the two X regions as described below, or may be cyclicized as described below. In this embodiment, each HBGF analog of the present invention can bind two HBGFRs and induce receptor dimerization. Advantageously, the dimerization in turn potentiates enhanced receptor signaling activity of the HBGFRs.

When n is 0 in formula I, the X region of the synthetic HBGF analog of the invention is covalently linked through an amino acid, $R_1$, to the region Y. Y may optionally be a hydrophobic region. Similarly, when n is 0 in formula II, the X region of the synthetic HBGF analog of the invention is covalently linked through an amino acid, $J_1$, to the region Y, but on the proviso that X is linked through a reactive side chain of $J_1$, and $J_1$ thus constitutes a trifunctional amino acid residue, such as a diamine amino acid. Here too Y may optionally be a hydrophobic region.

When n is 1 in formula I, one X region is covalently linked through an amino acid $R_1$, which is in turn covalently linked to a second amino acid, $R_2$, which is a trifunctional alpha amino acid, and preferably a diamine amino acid. $R_1$ is linked to one amino group of $R_2$. The second X region is covalently linked to $R_2$ through a second reactive group of $R_2$, such as the second amino group of a diamine amino acid. $R_2$ is then covalently linked through its carboxy terminus to the Y region of the synthetic HBGF analog. Similarly, when n is 1 in formula II, one X region is covalently linked through a reactive side chain of an amino acid $J_1$, which is in turn covalently linked to a second amino acid, $J_2$, both $J_1$ and $J_2$ constituting trifunctional amino acids, preferably diamine amino acids. The second X region is covalently linked to $J_2$ through a second reactive group of $J_2$, such as the second amino group of a diamine amino acid. $R_2$ is then covalently linked through its carboxy terminus to the Y region of the synthetic HBGF analog.

The amino acid $R_1$ of formula I can be any of the amino acids described above. $R_2$ of formula I, and $J_1$ and $J_2$ of formula II, can be any trifunctional amino acid residue, preferably a trifunctional alpha amino acid residue. In a preferred embodiment, the trifunctional amino acid residue is a diamine amino acid, such as for instance lysine or ornithine, or any other amino acid having two amino groups.

The region X of formulas I to IV of the synthetic HBGF analogs of the present invention is a synthetic peptide chain that binds an HBGFR. Region X can, for example, have any amino acid sequence that binds an HBGFR, and can include amino acid sequences that are identical to a portion of the amino acid sequence of a HBGF. Alternatively, X can have an amino acid sequence homologous rather than identical to the amino acid sequence of an HBGF. The particular HBGFR bound by the synthetic HBGF analog of the invention may or may not be the cognate receptor of the original HBGF, i.e. the synthetic HBGF analog may additionally or solely bind to the receptor of a different HBGF.

The term 'homologous', as used herein refers to peptides that differ in amino acid sequence at one or more amino acid positions when the sequences are aligned. For example, the amino acid sequences of two homologous peptides can differ only by one amino acid residue within the aligned amino acid sequences of five to ten amino acids. Alternatively, two homologous peptides of ten to fifteen amino acids can differ by no more than two amino acid residues when aligned. In another alternative, two homologous peptides of fifteen to twenty or more amino acids can differ by up to three amino acid residues when aligned. For longer peptides, homologous peptides can differ by up to approximately 5%, 10%, 20% or 25% of the amino acid residues when the amino acid sequences of the two peptide homologs are aligned.

Particularly useful amino acid sequences as X regions of formulas I to IV include homologs of fragments of naturally occurring HBGFs that differ from the amino acid sequences of natural growth factor in only one or two or a very few positions. Such sequences preferably include conservative changes, where the original amino acid is replaced with an amino acid of a similar character according to well known principles; for example, the replacement of a non-polar amino acid such as alanine with valine, leucine, isoleucine or proline; or the substitution of one acidic or basic amino acid with another of the same acidic or basic character.

In another alternative, the X region of the synthetic HBGF analog can include an amino acid sequence that shows no detectable homology to the amino acid sequence of any HBGF. Peptides or growth factor analogs useful as components of the X region of the synthetic analogs of the present invention, that have little or no amino acid sequence homology with the cognate growth factor and yet bind HBGFRs may be obtained by any of a wide range of methods, including for instance, selection by phage display. See as an example: Sidhu et al. Phage display for selection of novel binding peptides. Methods Enzymol. 328:333-63 (2000). An example of such a peptide that binds an HBGFR yet has no homology to any known HBGF is the C19 peptide sequence described below in Example 1.

The X region of the synthetic HBGF analogs of the invention can have any length that includes an amino acid sequence that effectively binds an HBGFR. Preferably, the X regions of the synthetic HBGF analogs have a minimum length of at least approximately three amino acid residues. More preferably, the X regions of the synthetic HBGF analogs have a minimum length of at least approximately six amino acid residues. Most preferably the X regions of the synthetic HBGF analogs have a minimum length of at least approximately ten amino acid residues. The X regions of the synthetic HBGF analogs of the invention preferably also have a maximum length of up to approximately fifty amino acid residues, more preferably a maximum length of up to approximately forty amino acid residues, and most preferably a maximum length of up to approximately thirty amino acid residues.

In one embodiment of the synthetic HBGF analogs that include two X regions, the X regions are covalently cross-linked. Suitable cross links can be formed by S—S bridges of cysteines linking the two X regions. Alternatively, the cross link can be conveniently formed during simultaneous and parallel peptide synthesis of the X region amino acids chains by incorporating a lanthionine (thio-dialanine) residue to link the two identical X chains at alanine residues that are covalently bonded together by a thioether bond. In another method the two X region amino acid chains can be cross-linked by introducing a cross-linking agent, such as a dicarboxylic acid, e.g. suberic acid (octanedioic acid), or the like, thereby introducing a hydrocarbon bridge between the two identical X regions having a free amino, hydroxyl or thiol group. The cross-linked X regions can constitute a cyclic peptide, such as where the terminal amino acids of X are cross-linked through reactive side chains or the terminal groups, optionally with a bridge or other link.

In the synthetic HBGF analogs of the present invention, in one preferred embodiment the Y region of formulas I to IV is a linker that is sufficiently hydrophobic to non-covalently bind the HBGF analog to a polystyrene or polycaprolactone surface, or the like. In addition, the Y region may bind to other hydrophobic surfaces, particularly the hydrophobic surfaces formed from materials used in medical devices. Such surfaces are typically hydrophobic surfaces. Examples of suitable surfaces include but are not limited to those formed from hydrophobic polymers such as polycarbonate, polyester, polypropylene, polyethylene, polystyrene, polytetrafluoroethylene, expanded polytetrafluoroethylene, polyvinyl chloride, polyamide, polyacrylate, polyurethane, polyvinyl alcohol, polyurethane, poly ethyl vinyl acetate, poly(butyl methacrylate), poly(ethyleneco-vinyl acetate), polycaprolactone, polylactide, polyglycolide and copolymers of any two or more of the foregoing; siloxanes such as 2,4,6,8-tetramethylcyclotetrasiloxane; natural and artificial rubbers; glass; and metals including stainless steel, titanium, platinum, and nitinol. Preferably, the binding of the HBGF analogs to the hydrophobic surface is of sufficient quantity to be detected by an analytical method such as an enzyme-linked immunoassay or a biological assay.

The Y region of formulas I to IV can include a chain of atoms or a combination of atoms that form a chain. Typically, the chains are chains of carbon atoms, that may also optionally include oxygen, nitrogen or sulfur atoms, such as for example chains of atoms formed from amino acids (e.g. amino acids found in proteins, as listed above; naturally occurring amino acids not found in proteins, such as ornithine and citrulline; or non natural amino acids, such as amino hexanoic acid; or a combination of any of the foregoing amino acids).

The chain of atoms of the Y region of formula I is covalently attached to $R_1$ or $R_2$ and to peptide Z. Similarly the chain of atoms of the Y region of formula II is covalently attached to $J_1$ or $J_2$ and to peptide Z. The covalent bonds can be, for example, peptide, amide or ester bonds. Preferably, the Y region includes a chain of a minimum of about nine atoms. More preferably, the Y region includes a chain of a minimum of about twelve atoms. Most preferably, the Y region includes a chain of a minimum of about fifteen atoms. For example, the Y region may be formed from a chain of at least four, at least five or at least six amino acids. Alternatively, the Y region may be formed from a chain of at least one, at least two, or at least three aminohexanoic acid residues.

Preferably, the Y region includes a chain of a maximum of about fifty atoms. More preferably, the Y region includes a chain of a maximum of about forty-five atoms. Most preferably, the Y region includes a chain of a maximum of about thirty-five atoms. For example, the Y region may be formed from a chain of up to about twelve, up to about fifteen, or up to about seventeen amino acids.

The amino acid sequence of the Y region of formula I or II is preferably an artificial sequence, i.e. it does not include any amino acid sequence of four or more amino acid residues found in a natural ligand of a HBGF.

In a particular embodiment, the Y region includes a hydrophobic amino acid residue, or a chain of hydrophobic amino acid residues. The Y region can, for example, include one or more aminohexanoic acid residues, such as one, two, three or more aminohexanoic acid residues.

In another particular embodiment, the Y region of the molecule of formula I or II can include a branched or unbranched, saturated or unsaturated alkyl chain of between one and about twenty carbon atoms. In a further embodiment, the Y region can include a chain of hydrophobic residues, such as for instance, ethylene glycol residues. For instance, the Y region can include at least about three, or at least about four, or at least about five ethylene glycol residues. Alternatively, the Y region can include up to about twelve, up to about fifteen, or up to about seventeen ethylene glycol residues. In another alternative embodiment, the Y region can include a combination of amino acid hydrophobic residues.

The Z region of the molecule of formula I or II is a heparin-binding region and can include one or more heparin-binding motifs, BBxB or BBBxxB as described by Verrecchio et al. J.Biol.Chem. 275:7701 (2000). Alternatively, the Z region can include both BBxB and BBBxxB motifs (where B represents lysine, arginine, or histidine, and x represents a naturally occurring, or a non-naturally occurring amino acid). For example, the heparin-binding motifs may be represented by the sequence [KR][KR][KR]X(2)[KR] (SEQ ID NO:1), designating the first three amino acids as each independently selected from lysine or arginine, followed by any two amino acids and a sixth amino acid which is lysine or arginine.

The number of heparin binding motifs is not critical. For instance, the Z region may include at least one, at least two, at least three or at least five heparin-binding motifs. Alternatively, the Z region may include up to a maximum of about ten heparin-binding motifs. In another alternative embodiment, the Z region includes at least four, at least six or at least eight amino acid residues. Further, the Z region may include up to about twenty, up to about, twenty-five, or up to about thirty amino acid residues. It is to be realized that, in part, the avidity of the Z region for heparin is determined by the particular heparin-binding motifs selected and the number of such motifs in Z. Thus for particular applications both the selection and number of such motifs may be varied to provide optimal heparin binding of the Z region.

In a preferred embodiment, the amino acid sequence of the Z region is RKRKLERIAR (SEQ ID NO:2). In another embodiment, the amino acid sequence of the Z region is RKRKLGRIAR (SEQ ID NO:3). In yet another embodiment, the amino acid sequence of the Z region is RKRKLWRARA (SEQ ID NO:4). In yet another embodiment, the amino acid sequence of the Z region is RKRKLERIARC (SEQ ID NO:5). The presence of a terminal cysteine residue optionally affords the opportunity to link other molecules, including detection reagents such as fluorochromes, radioisotopes and other detectable markers, to the Z region, as well as the opportunity to link toxins, immunogens and the like.

Heparin-binding domains that bear little or no sequence homology to known heparin-binding domains are also contemplated in the present invention. As used herein the term "heparin-binding" means binding to the $—NHSO_3^-$ and sulfate modified polysaccharide, heparin, and also binding to the related modified polysaccharide, heparan.

The Z region of the synthetic HBGF analogs of the present invention confers the property of binding to heparin in low salt concentrations, up to about 0.15 M NaCl, optionally up to about 0.48 M NaCl, forming a complex between heparin and the Z region of the factor analog. The complex can be dissociated in 1 M NaCl to release the synthetic HBGF analog from the heparin complex.

The Z region is a non-signaling peptide. Accordingly, when used alone the Z region binds to heparin which can be bound to a receptor of a HBGF, but the binding of the Z region peptide alone does not initiate or block signaling by the receptor.

The C-terminus of the Z region may be blocked or free. For example, the C terminus of the Z region may be the free carboxyl group of the terminal amino acid, or alternatively, the C terminus of the Z region may be a blocked carboxyl group, such as for instance, an amide group. In a preferred embodiment the C terminus of the Z region is an amidated arginine as shown in FIGS. 1 and 2.

As used here and elsewhere, the following terms have the meanings given.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like. The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A peptide or aliphatic moiety is "acylated" when an alkyl or substituted alkyl group as defined above is bonded through one or more carbonyl {—(C═O)—} groups. A peptide is most usually acylated at the N-terminus.

An "amide" includes compounds that have a trivalent nitrogen attached to a carbonyl group (—$CO.NH_2$).

An "amine" includes compounds that contain an amino group (—$NH_2$).

FGF Synthetic Analogs

In another particular aspect, the invention provides a synthetic FGF peptide analog. The synthetic FGF analogs represented by any of formulas I to IV above, wherein X is an FGF analog, is an analog of an FGF which can be any FGF, such as any of the known FGFs, including all 23 FGFs from FGF-1 to FGF-23.

The X region of the molecule of formulas I to IV can include an amino acid sequence found in an FGF, such as for instance FGF-2 or FGF-7. Alternatively, the X region can include a sequence not found in the natural ligand of the FGFR bound by the molecule.

The Y region of the synthetic FGF peptide analogs of any of formulas I to IV are not necessarily hydrophobic, and thus, if present, can be polar, basic, acidic, hydrophilic or hydrophobic. Thus, the amino acid residues of the Y region of synthetic FGF peptide analogs can include any amino acid, or polar, ionic, hydrophobic or hydrophilic group.

The X region of synthetic FGF peptide analogs can include an amino acid sequence that is 100% identical to the amino acid sequence found in a fibroblast growth factor or an amino acid sequence homologous to the amino acid sequence of a fibroblast growth factor. For instance, the X region can include an amino acid sequence that is at least about 50%, at least about 75%, or at least about 90% homologous to an amino acid sequence from a fibroblast growth factor. The fibroblast growth factor can be any fibroblast growth factor, including any of the known or yet to be identified fibroblast growth factors.

In a particular embodiment, the synthetic FGF analog of the invention is an agonist of the HBGFR. When bound to the HBGFR, the synthetic HBGF analog initiates a signal by the HBGFR.

In a further particular embodiment, the synthetic FGF analog of the invention is an antagonist of the HBGFR. When bound to the HBGFR, the synthetic HBGF analog blocks signaling by the HBGFR.

In another particular embodiment of the present invention, the synthetic FGF analog is an analog of FGF-2 (also known as basic FGF, or bFGF). In another particular embodiment of the present invention, the binding of the synthetic FGF analog to an FGF receptor initiates a signal by the FGF receptor. In a further particular embodiment, the binding of the synthetic FGF analog to the FGF receptor blocks signaling by the FGF receptor.

In a yet further particular embodiment, the present invention provides a synthetic FGF analog of FGF-2, wherein the FGF receptor-binding domain is coupled through a hydrophobic linker to a heparin-binding domain. In another particular embodiment, the present invention provides a synthetic FGF analog of FGF-2, wherein the amino acid sequence of the X region is YRSRKYSSWYVALKR (SEQ ID NO:6) from FGF-2. In yet another particular embodiment, the present invention provides a synthetic FGF analog wherein the amino acid sequence of the X region is NRFHSWDCIKTWASDTFVLVCYDDGSEA (SEQ ID NO:7).

In a yet further particular embodiment, the invention provides a synthetic FGF analog of FGF-1, wherein the X region is YISKKHAEKNWFVGLKK (SEQ ID NO:8). This sequence is derived from amino acids bridging the beta 9 and beta 10 loop of FGF-1. In yet another particular embodiment, an FGF-1 analog is provided wherein the X region is HIQLQLSASEVGEVY (SEQ ID NO:9), corresponding to amino acids derived from the β-4 and β-5 region of FGF-1.

In a yet further particular embodiment, the invention provides a synthetic FGF analog of FGF-7, wherein the X region is YASAKWTHNGGEMFVALNQK (SEQ ID NO:10). In yet another embodiment of a synthetic FGF analog of FGF-7, the X regions is the amino acid sequence YNIMEIRTVAVGIVA (SEQ ID NO:11).

Table 1 below compares the actions of two synthetic FGF analogs of the present invention, F2A3 and F2A4, with that of recombinant FGF-2. In growth studies, the specific cell lines that were used included murine C3H10T1/2 fibroblasts, A7R5 murine smooth muscle cells, human umbilical vein endothelial cells (HUVEC), bovine aorta endothelial cells (BAE), rat microvascular endothelial cells (RMEC), and CG4 glioma cells. Changes in smooth muscle actin and TGF-βRII (receptor for transforming growth factor-beta) were monitored by immunochemistry. Nitric oxide (NO) production was monitored by fluorescence microscopy using 2,4-diaminofluorescein as the fluorogen. Angiogenesis was monitored following introduction of coated sutures in rat muscle. Salivary gland stimulation was determined by monitoring saliva production. Wound healing was monitored in full thickness wounds of rat skin. In Table 1 and hereafter, "N.D." means not determined.

TABLE 1

|  | FGF-2 | F2A3 | F2A4 |
|---|---|---|---|
| Biochemical |  |  |  |
| Interaction with heparin | Yes | Yes | Yes |
| Binding to FGF receptor | Yes | Yes | Yes |
| Binding to VEGF receptor | No | No | No |
| MAP kinase phosphorylation and activation | Yes | Yes | Yes |
| Growth stimulation |  |  |  |
| Fibroblasts, Endothelial cells, Smooth muscle cells, Neural cells | Yes | Yes | Yes |
| Cellular changes |  |  |  |
| Increased smooth muscle cell actin | Yes | Yes | Yes |
| Increased NO production, endothelial cells | Yes | Yes | N.D. |
| Decreased TGF-β RII, endothelial cells | Yes | Yes | N.D. |
| Radiation protection | Yes | Yes | Yes |
| In vivo |  |  |  |
| Angiogenisis | Yes | Yes | Yes |
| Radiation protection, in vivo | Yes | Yes | Yes |
| Salivary gland stimulation | Yes | Yes | N.D. |
| Accelerated skin wound healing | Yes | Yes | N.D. |

VEGF Synthetic Analogs

In another particular aspect, the invention provides a synthetic VEGF peptide analog. The synthetic VEGF analogs represented include, in one embodiment, a VEGF analog wherein the amino acid sequence of the X region is APMAEGGGQNHHEVVKFMDV (SEQ ID NO:12). In another embodiment, there is provided a synthetic VEGF peptide analog wherein the amino acid sequence of the X region is GATWLPPNPTK (SEQ ID NO:13). In yet another embodiment, there is provided a synthetic VEGF peptide analog wherein the amino acid sequence of the X region is NFLLSWVHWSLALLLYLHHA (SEQ ID NO:14).

Table 2 below compares the actions of two synthetic VEGF peptide analogs of the present invention, VA01 and VA02, with that of recombinant VEGF. For MAP kinase, bovine aorta endothelial (BAE) cells were stimulated with 50 ng/mL of VEGF, VA01 or VA02 for 30 or 60 minutes. Cell lysate was analysed by Western blotting using monoclonal anti-phospho-44/42 MAP kinase antibody (Thr202 and Tyr204) and increased phosphorylization of ERK-1 and ERK-2 relative to controls was detected following stimulation with VEGF, VA01 or VA02. For growth, an increase in relative cell number of BAE cells was found following stimulation with VEGF, VA01 or VA02 whereas in A7R5, a smooth muscle cell line, no growth stimulation was found, indicating specificity in the action of the analogs.

TABLE 2

|  | VEGF | VA01 | VA02 |
|---|---|---|---|
| Biochemical |  |  |  |
| Interaction with heparin | Yes | Yes | Yes |
| MAP kinase phosphorylation | Yes | Yes | Yes |
| Growth stimulation |  |  |  |
| Endothelial cells | Yes | Yes | Yes |
| Smooth muscle cells | No | No | No |
| Cellular changes |  |  |  |
| Tube formation in collagen gels (in vitro model of angiogenisis) | Yes | Yes | Yes |

BMP Synthetic Analogs

In another particular aspect, the invention provides a synthetic BMP peptide analog. The synthetic bone morphogenic protein analogs include embodiments wherein the X region is the amino acid sequence LYVDFSDVGWNDW (SEQ ID NO:15), AISMLYLDENEKVVL (SEQ ID NO:16), ISMLYLDENEKVVLKNY (SEQ ID NO:17), EKVVLKNYQDMVVEG (SEQ ID NO:18), LVVKENEDLYLMSIAC (SEQ ID NO:19), AFYCHGECPFPLADHL (SEQ ID NO:20), or PFPLADHLNSTNHAIVQTLVNSV (SEQ ID NO:21).

Table 3 below summarizes the biochemical interactions of one BMP analog, B2A2, and the modulation of alkaline phosphatase, wherein modulation was monitored using C2C12 cells.

TABLE 3

| Biochemical interactions of B2A2 |  |
|---|---|
| Interaction with heparin | Yes |
| MAP kinase phosphorylation | Yes |
| Positive modulation of alkaline phosphatase |  |
| BMP-2 (E. coli) | Yes |
| BMP-2 (Chinese hamster ovary cells) | Yes |
| BMP-7 (mammalian cell) | No |
| Modulation via a coating of alkaline phosphatase |  |
| B2A2 coating, BMP-2 in solution | Yes |
| BMP-2 coating, B2A2 in solution | Yes |
| Silyl-heparin/BMP-2 coating, B2A2 in solution | Yes |

Methods of Synthesizing the Heparin-Binding Growth Factor Analogs

The synthesis of the analogs of the invention can be achieved by any of a variety of chemical methods well known in the art. Such methods include bench scale solid phase synthesis and automated peptide synthesis in any one of the many commercially available peptide synthesizers. Preferably, the synthesizer has a per cycle coupling efficiency of greater than 99 percent.

The analogs of the present invention can be produced by stepwise synthesis or by synthesis of a series of fragments that can be coupled by similar well known techniques. See, for instance, Nyfeler, Peptide synthesis via fragment condensation. Methods Mol Biol 35:303-16 (1994); and Merrifield, Concept and early development of solid-phase peptide synthesis. Methods in Enzymol 289:3-13 (1997). These methods are routinely used for the preparation of individual peptides. It is possible to assemble the analogs of the present invention in component parts, such as peptides constituting the X, Y and Z components thereof, and to thereafter couple such component parts to assemble the analog. See, for instance, Dawson and Kent, Synthesis of native proteins by chemical ligation. Annu. Rev. Biochem. 69:923-960 (2000); and Eom et al., Tandem ligation of multipartite peptides with cell-permeable activity. J. Am. Chem. Soc. 125:73-82 2003).

Advantageously, in the case where the analogs of formulas I to IV of the invention include two identical X region amino acid sequences, the synthesis of these identical X region peptides may be performed in parallel. By this method each cycle of addition adds an amino acid to both of the X region peptides, greatly facilitating the synthesis of these branched molecules.

Peptide libraries that can be used to screen for a desired property, such as binding to an HBGFR can be prepared by adaptations of these methods. See for instance, Fox, Multiple peptide synthesis, Mol. Biotechnol. 3:249-58 (1995); and Wade and Tregear, Solid phase peptide synthesis: recent advances and applications. Austral. Biotechnol. 3:332-6 (1993).

In a particular embodiment, the synthetic HBGF analog of the invention is an agonist of the HBGFR. When bound to the HBGFR, the synthetic HBGF analog initiates a signal by the HBGFR.

In another particular embodiment, the synthetic HBGF analog of the invention is an antagonist of the HBGFR. When bound to the HBGFR, the synthetic HBGF analog blocks signaling by the HBGFR.

In a particular aspect, the invention provides a method for stimulating growth factor receptor signaling in a cell by contacting the cell with an effective amount of a synthetic HBGF analog according to formulas I to IV. The effective amount can be readily determined by one of skill in the art. The signaling can result in cytokine release from the cell, stimulation or inhibition of proliferation or differentiation of the cell, chemotaxis of the cell, stimulation or inhibition of the immune system of the mammal.

Methods of Use of the HBGFs of the Invention

The HBGF analogs of the invention provide a cost effective and potentially unlimited source of biologically active molecules that are useful in a number of ways, including as soluble prophylactic or therapeutic pharmaceutical agents, such as for instance for administration as a soluble drug for prevention or treatment of various diseases, including for example, uses in cancer therapy and radioprotection.

The synthetic HBGF analogs of present invention are also useful as biologically active agents for coating of medical devices, such as for instance, sutures, implants and medical instruments to promote biological responses, for instance, to stimulate growth and proliferation of cells, or healing of wounds.

In one aspect, the present invention provides a method for treating a mammal that has been exposed to a harmful dose of radiation. The method includes administering an effective dose of a synthetic HBGF analog of the invention which is an FGF analog to the mammal. The treatment is particularly useful in the prevention or treatment of mucositis, gastrointestinal syndrome (G.I. syndrome), or radionecrosis such as can result from exposure to radiation. The HBGF analog can be administered parenterally, orally, or topically. Alternatively, the HBGF analog can be delivered loco-regionally, e.g. on an analog coated medical device. In a related embodiment, the present invention provides a method for treating a mammal that has been administered a dose of a chemotherapeutic agent, to ameliorate the toxicity of the chemotherapeutic agent to the mammal. In a particular embodiment of the above-described methods, the mammal is a human. In another particular embodiment of the method, the HBGF analog is an FGF-2 analog or an FGF-7 analog.

The term "medical device" as used herein means a device that has one or more surfaces in contact with an organ, tissue, blood or other bodily fluid in an organism, preferably a mammal, particularly, a human. Medical devices include, for example, extracorporeal devices for use in surgery such as blood oxygenators, blood pumps, blood sensors, tubing used to carry blood, and the like which contact blood that is returned to the patient. The term can also include endoprostheses implanted in blood contact in a human or animal body, such as vascular grafts, stents, pacemaker leads, heart valves, and the like that are implanted in blood vessels or in the heart. The term can further include devices for temporary intravascular use such as catheters, guide wires, and the like that are placed in blood vessels or the heart for purposes of monitoring or repair. The term can further include nerve electrodes, muscle electrodes, implantable pulse generators, implantable drug pumps, and defibrillators. Moreover, the term medical device can include sutures, graft materials, wound coverings, nerve guides, bone wax, aneurysm coils, embolization particles, microbeads, dental implants, bone prostheses, tissue scaffolds, artificial joints or a controlled release drug delivery devices.

The surface of the medical device can be formed from any of the commonly used materials suitable for use in medical devices, such as for instance, stainless steel, titanium, platinum, tungsten, ceramics, polyurethane, polytetrafluoroethylene, extended polytetrafluoroethylene, polycarbonate, polyester, polypropylene, polyethylene, polystyrene, polyvinyl chloride, polyamide, polyacrylate, polyurethane, polyvinyl alcohol, polycaprolactone, polylactide, polyglycolide, polysiloxanes (such as 2,4,6,8-tetramethylcyclotetrasiloxane), natural rubbers, or artificial rubbers, or block polymers or copolymers thereof.

Methods for coating biological molecules onto the surfaces of medical devices are known. See for instance U.S. Pat. No. 5,866,113 to Hendriks et al., the specification of which is hereby incorporated by reference. Tsang et al. in U.S. Pat. No. 5,955,588 teach a non-thrombogenic coating composition and methods for using the same on medical devices, and is incorporated herein by reference. Zamora et al. in U.S. Pat. No. 6,342,591 teach an amphipathic coating for medical devices for modulating cellular adhesion composition, and is incorporated herein by reference.

Other coating inventions that teach away from the current invention include the following: Ottersbach et al. in U.S. Pat. No. 6,248,811 teach a bioactive coating that covalently fixes coatings on the surfaces of substrates, and therefore teaches away from the current invention. Ragheb et al. in U.S. Pat. No. 6,299,604 describes a coating layer posited on one surface of the structure wherein a bioactive material is posited on at least a portion of the coating layer and diffuses out through a porous layer. Similarly, Chudzik et al. in U.S. Pat. No. 6,344,035 describes a bioactive agent release coating that includes a bioactive agent in combination with a mixture of a polymer component. Sprague in U.S. Pat. No. 6,140,127 describes a method of coating an intravascular stent with an endothelial cell adhesive five amino acid peptide. This coating is preferably carried out by activating the intravascular stent using plasma glow discharge, applying an additional layer(s), applying a tresylation solution containing pyridine and tresyl chloride, and applying a five amino acid peptide having the sequence glycine-arginine-glutamic acid-aspartic acid-valine to result in chemical conjugation of the peptide to the surface. Steber et al. in U.S. Pat. No. 5,801,141 teach an implant for the parenteral administration of an essentially uniform and continuous amount of a biologically active protein, a peptide or a polypeptide which comprises a compacted, indented and partially coated composition containing from one to three layers of a homogeneous core mixture comprising about 20% to about 80% of the growth factor, the biologically active fragment or the derivative; about 10% to about 75% of a fat, a wax or a mixture thereof; 0% to about 25% of a buffer, a salt, a sugar or a mixture thereof; and 0% to about 15% of a filler, on a weight basis of the total weight of the core mixture.

In one embodiment the invention provides a method for delivering an active peptide to a mammal, the method includes (i) providing a medical device coated on its surface with a synthetic HBGF analog of formulas I to IV, the synthetic HBGF analog being bound to the surface of the medical device by non-covalent bonds; and (ii) placing the medical device onto a surface of, or implanting the medical device into, the mammal.

In a particular embodiment of the above method, the non-covalent bonds are associations between the heparin binding domain of the synthetic HBGF analog and a heparin-containing compound bound to the surface of the medical device. The heparin-containing compound bound to the surface of the medical device can be any heparin-containing compound, such as for instance, benzyl-bis(dimethylsilylmethyl)oxy carbamoyl-heparin.

In another particular embodiment of the above method, the medical device is not pre-coated with a heparin-containing compound before being coated with the synthetic HBGF analog of formulas I to IV.

Heparin-Binding Growth Factors

The fibroblast growth factors, FGFs constitute a family of related proteins controlling normal growth and differentiation of mesenchymal, epithelial, and neuroectodermal cell types. Homologs have been found in a wide variety of species. FGFs show a very high affinity to heparin and are therefore also referred to as heparin-binding growth factors (HBGFs). As used herein, the term HBGFs includes all FGFs.

Two main types of FGF are known. The first type of FGF was isolated initially from brain tissue. It was identified by its proliferation-enhancing activities for murine fibroblasts, such as 3T3 cells. Due to its basic pI the factor was named basic FGF (bFGF, or HBGF-2, heparin-binding growth factor-2) and is now generally referred to as FGF-2. This is the prototype of the FGF family.

Another type of FGF, also initially isolated from brain tissues, is acidic FGF (aFGF, also known as HBGF-1, heparin-binding growth factor-1 or HBGF-α, heparin-binding growth factor-α), now generally referred to as FGF-1. It was identified by its proliferation-enhancing activity for myoblasts.

Other fibroblast growth factors belonging to the same family include FGF-3 (or HBGF-3, heparin-binding growth factor-3, originally called int-2; see Fekete, Trends in Neurosci. 23:332 (2000)), FGF-4 (HBGF-4, heparin-binding growth factor-4, initially recognized as the product of the oncogene hst; see Sakamoto et al., Proc. Natl. Acad. Sci. USA 91:12368-72), and FGF-5 (originally called HBGF-5, see Bates et al. Biosynthesis of human fibroblast growth factor 5. Mol. Cell. Biol. 11:1840-1845 (1991)); Burgess and Maciag, The heparin-binding (fibroblast) growth factor family of proteins. Ann. Rev. Biochem. 58: 575-606 (1989); and Zhan et al. The human FGF-5 oncogene encodes a novel protein related to fibroblast growth factors. Mol. Cell. Biol. 8:3487-3495 (1988)).

FGF-6 is also known as HBGF-6, and sometimes called hst-2 or oncogene hst-1 related growth factor, see Iida et al. Human hst-2 (FGF-6) oncogene: cDNA cloning and characterization. Oncogene 7:303-9 (1992); and Marics et al. Characterization of the HST-related FGF-6 gene, a new member of the fibroblast growth factor gene family. Oncogene 4:335-40 (1989).

FGF-7 or K-FGF is also known as KGF or keratinocyte growth factor (See Aaronson et al. Keratinocyte growth factor. A fibroblast growth factor family member with unusual target cell specificity. Annals NY Acad. Sci. 638:62-77 (1991)); Finch et al. Human KGF is FGF-related with properties of a paracrine effector of epithelial cell growth. Science 245:752-5 (1989); Marchese et al. Human keratinocyte growth factor activity on proliferation and differentiation of human keratinocytes: differentiation response distinguishes KGF from EGF family. J. Cellular Physiol. 144: 326-32 (1990)).

FGF-8 was found to be identical to androgen-induced growth factor, AIGF and has been well studied (See Blunt et al. Overlapping expression and redundant activation of mesenchymal fibroblast growth factor (FGF) receptors by alternatively spliced FGF-8 ligands. J. Biol. Chem. 272:3733-8 (1997)); Dubrulle et al. FGF signaling controls somite boundary position and regulates segmentation clock control of spatiotemporal Hox gene activation. Cell 106:219-232 (2001); Gemel et al. Structure and sequence of human FGF8. Genomics 35:253-257 (1996); Tanaka et al. A novel isoform of human fibroblast growth factor 8 is induced by androgens and associated with progression of esophageal carcinoma. Dig. Dis. Sci. 46:1016-21 (2001)).

FGF-9 was originally called glia activating factor, or HBGF-9. See Miyamoto et al. Molecular cloning of a novel cytokine cDNA encoding the ninth member of the fibroblast growth factor family, which has a unique secretion pattern. Mol. Cell. Biol. 13:4251-9 (1993); and Naruo et al. Novel secretory heparin-binding factors from human glioma cells (glia-activating factors) involved in glial cell growth. J. Biol. Chem. 268: 2857-64 (1993).

FGF-10 is also called KGF-2, keratinocyte growth factor-2 (see Kok et al. Cloning and characterization of a cDNA encoding a novel fibroblast growth factor preferentially expressed in human heart. Biochem. Biophys. Res. Comm. 255:717-721, (1999)).

Several FGF-related factors have been described as fibroblast growth factor homologous factors (FHFs) and are also referred to as FGF-11 (FHF-3), FGF-12 (FHF-1), FGF-13 (FHF-2, see Greene et al. Identification and characterization of a novel member of the fibroblast growth factor family. Eur. J. Neurosci. 10:1911-1925 (1998)), and FGF-14 (FHF-4).

FGF-15 is expressed in the developing nervous system and was identified as a gene regulated by transcription factor E2A-Pbx1. McWhirter et al. A novel fibroblast growth factor gene expressed in the developing nervous system is a downstream target of the chimeric homeodomain oncoprotein E2A-Pbx1. Development 124:3221-3232 (1997).

FGF-16 was isolated as a cDNA clone from rat heart by homology-based polymerase chain reaction expressing an FGF of 207 amino acids. FGF-16 is 73% identical to FGF-9. Miyake et al. Structure and expression of a novel member, FGF-16, of the fibroblast growth factor family. Biochem. Biophys. Res. Commun. 243:148-152 (1998).

The cDNA encoding FGF-17 was isolated from rat embryos and encodes a protein of 216 amino acids. When expressed in 3T3 fibroblasts, mouse FGF-17 is transforming. During embryogenesis, FGF-17 is expressed at specific sites in forebrain, the midbrain-hindbrain junction, the developing skeleton and in developing arteries. See Hoshikawa et al. Structure and expression of a novel fibroblast growth factor, FGF-17, preferentially expressed in the embryonic brain. Biochem. Biophys. Res. Commun. 244:187-191 (1998); and Xu et al. Genomic structure, mapping, activity and expression of fibroblast growth factor 17. Mechanisms of Development 83:165-178 (1999).

The cDNA encoding FGF-18 was isolated from rat embryos encoding a protein of 207 amino acids. FGF-18 is a glycosylated protein and is most similar to FGF-8 and FGF-17. Injection of recombinant murine FGF-18 has been shown to induce proliferation in tissues of both epithelial and mesenchymal origin, particularly in liver and small intestine. Recombinant rat FGF-18 induces neurite outgrowth in PC12 cells. Recombinant murine FGF-18 protein stimulates proliferation in NIH 3T3 fibroblasts in vitro in a heparan sulfate-dependent manner. For general information see Hu et al. FGF-18, a novel member of the fibroblast growth factor family, stimulates hepatic and intestinal proliferation. Mol. Cell. Biol. 18:6063-6074 (1998); and Ohbayashi et al. Structure and expression of the mRNA encoding a novel fibroblast growth factor, FGF-18. J. Biol. Chem. 273:18161-18164 (1998).

FGF-19 is related distantly to other members of the FGF family. FGF-19 mRNA is expressed in several tissues including fetal cartilage, skin, and retina, as well as adult gall bladder. It is overexpressed in a colon adenocarcinoma cell line. FGF-19 is a high affinity, heparin-dependent ligand for the FGF-4 receptor. See Xie et al. FGF-19, a novel fibroblast growth factor with unique specificity for FGFR4 Cytokine 11:729-735 (1999).

FGF-20 is expressed in normal brain, particularly the cerebellum, and in some cancer cell lines. FGF-20 mRNA is expressed preferentially in the substantia nigra pars compacta. Recombinant FGF-20 protein induces DNA synthesis in a variety of cell types and is recognized by multiple FGF receptors. FGF-20 functions like an oncogene, causing a transformed phenotype when expressed in the 3T3 fibroblast cell line. These transformed cells are tumorigenic in nude mice. See Jeffers et al. Identification of a novel human fibroblast growth factor and characterization of its role in oncogenesis. Cancer Res. 61:3131-8 (2001); and Ohmachi et al. FGF-20, a novel neurotrophic factor, preferentially expressed in the substantia nigra pars compacta of rat brain. Biochem. Biophys. Res. Commun. 277:355-60 (2000).

FGF-21 was isolated from mouse embryos. FGF-21 mRNA is most abundant in the liver with lower levels in the thymus. FGF-21 is most similar to human FGF-19. See Nishimura et al. Identification of a novel FGF, FGF-21, preferentially expressed in the liver. Biochim. Biophys. Acta 1492:203-6 (2000).

The cDNA encoding FGF-22 (170 amino acids) was isolated from human placenta. FG-F22 is most similar to FGF-10 and FGF-7. Murine FGF-22 mRNA is expressed preferentially in the skin. FGF-22 mRNA in the skin is found preferentially in the inner root sheath of the hair follicle. See Nakatake et al. Identification of a novel fibroblast growth factor, FGF-22, preferentially expressed in the inner root sheath of the hair follicle. Biochim. Biophys. Acta 1517:460-3 (2001).

FGF-23 is most similar to FGF-21 and FGF-19. The human FGF-23 gene maps to chromosome 12p13 linked to human FGF-6 gene. FGF-23 mRNA is expressed mainly in the brain (preferentially in the ventrolateral thalamic nucleus) and thymus at low levels. Missense mutations in the FGF-23 gene have been found in patients with autosomal dominant hypophosphataemic rickets. Overproduction of FGF23 causes tumor-induced osteomalacia, a paraneoplastic disease characterized by hypophosphatemia caused by renal phosphate wasting. See Yamashita et al. Identification of a novel fibroblast growth factor, FGF-23, preferentially expressed in the ventrolateral thalamic nucleus of the brain. Biochem. Biophys. Res. Commun. 277:494-8 (2000); and Shimada et al. Cloning and characterization of FGF23 as a causative factor of tumor-induced osteomalacia. Proc. Natl. Acad. Sci. (USA) 98:6500-5 (2001).

HBBM (Heparin-binding brain mitogen) was isolated initially as a heparin binding protein from brain tissues of several species and is identical to heparin-binding neurite promoting factor. See Huber et al. Amino-terminal sequences of a novel heparin-binding protein with mitogenic activity for endothelial cells from human bovine, rat, and chick brain: high interspecies homology. Neurochem. Res. 15:435-439 (1990).

HB-GAF (heparin-binding growth associated factor) is a neurotrophic and mitogenic factor identical to HBNF (heparin-binding neurite-promoting factor). See Kuo et al. Characterization of heparin-binding growth-associated factor receptor in NIH 3T3 cells. Biochem. Biophys. Res. Commun. 182:188-194 (1992).

HB-EGF (heparin-binding EGF-like factor) is found in conditioned media of cell line U937 and is also synthesized by macrophages and human vascular smooth muscle cells. HB-EGF is a monomeric heparin-binding O-glycosylated protein of 86 amino acids and is processed from a precursor of 208 amino acids. Several truncated forms of HB-EGF have been described. HBEGF is a potent mitogen for NIH 3T3 cells, keratinocytes and smooth muscle cells, but not for endothelial cells. The mitogenic activity on smooth muscle cells is much stronger than for EGF and appears to involve interactions with cell surface heparan sulfate proteoglycans. HB-EGF is a major growth factor component of wound fluid and may play an important role in wound healing. See Abraham et al. Heparin-binding EGF-like growth factor: characterization of rat and mouse cDNA clones, protein domain conservation across species, and transcript expression in tissues. Biochem. Biophys. Res. Commun. 190:125-133 (1993); Higashiyama et al. A heparin-binding growth factor secreted by macrophage like cells that is related to EGF. Science 251:936-9 (1991); and Marikovsky et al. Appearance of heparin-binding EGF-like growth factor in wound fluid as a response to injury. Proc. Natl. Acad. Sci. (USA) 90:3889-93.

HB-GAM (heparin-binding growth associated molecule) also referred to as HBNF (heparin-binding neurite promoting factor) is a protein of 15.3 kDa isolated as a heparin binding protein from brain tissues of several species. HB-GAM promotes growth of SW-13 cells in soft agar. Courty et al. Mitogenic properties of a new endothelial cell growth factor related to pleiotrophin. Biochem. Biophys. Res. Commun. 180:145-151 (1991); and Hampton et al. Structural and functional characterization of full-length heparin-binding growth associated molecule. Mol. Biol. Cell. 3:85-93 (1992).

TGF-beta (TGF-β) exists in at least five isoforms, known TGF-β1, TGF-β2, TGF-β3, TGF-β4 and TGF-β5, that are not related to TGF-α. Their amino acid sequences display homologies on the order of 70-80 percent. TGF-β1 is the prevalent form and is found almost ubiquitously while the other isoforms are expressed in a more limited spectrum of cells and tissues.

TGF-beta is the prototype of a family of proteins known as the TGF-beta superfamily. This family includes inhibins, Activin A, MIS (Mullerian activating substance) and BMPs (Bone morphogenic proteins). Burt, Evolutionary grouping

EXAMPLES

Example 1

The synthetic HBGF analog, F2A3, the structure of which is shown in FIG. 1, was synthesized by standard solid phase peptide synthesis methods. F2A3 has a structure according to formula II, in which the amino acid sequences of the X region, NRFHSWDCIKTWASDTFVLVCYDDGSEA (SEQ ID NO:7), corresponds to the C19 peptide sequence identified by Ballinger et al. (Nature Biotechnology 17:1199 (1999)). Each of the two X region peptides of SEQ ID NO:7 are covalently linked by amide bonds to a lysine residue, the lysine residues corresponding to $J_1$ and $J_2$. The $J_2$ Lys is bound by means of a covalent peptide bond to one terminus of a tripeptide formed from three aminohexanoic acid residues and corresponding to linker Y, providing a hydrophobic space of 18 alkyl carbon atoms. The opposite terminus of the aminohexanoic acid tripeptide is covalently bound by a peptide bond to heparin-binding peptide RKRKLERIAR (SEQ ID NO:2) corresponding to region Z.

The peptides were assembled stepwise by solid-phase synthesis on a substituted benzhydrylamine resin, using Fmoc chemistry for temporary protection of amino groups in the repetitive cycles. Branching of the chain was accomplished by stepwise growth of identical chains from the side-chain amino groups of consecutive lysyl residues. The completed peptide chains were cleaved from the resin as C-terminal amides by acidolysis, which also removed the acid-labile side-chain protecting groups.

The crude peptide preparation was first purified by heparin affinity chromatography. The crude preparation was solubilized in 10 mM HEPES (pH 7.0), loaded onto a HiTrap® Heparin HP column (Amersham Pharmacia Biotech, Piscataway, N.J., USA), and washed with 10 column volumes of 10 mM HEPES (pH 7.0). The peptide was then eluted with 2 M NaCl in 10 mM HEPES (pH 7.0), monitored by 280 nm absorbance. Peptide fractions were desalted and concentrated by loading onto Sep-Pak® C18 cartridges (Waters, Milford, Mass., USA), washed with 10 column volumes of water, and then eluted with 80% acetonitrile. Eluted fractions were lyophilized, redissolved in water, and the concentration was determined by BCA® Protein Assay Kit (Pierce Endogen, Rockford, Ill., USA) using bovine serum albumin as a reference.

Example 2

The synthetic HBGF analog, F2A4, as shown in FIG. 2, was synthesized by standard solid phase peptide synthesis methods. The amino acid sequences of F2A4 corresponding to regions Y and Z of formula II are identical to those of F2A3 described in Example 1. The amino acid sequence YRSRKYSSWYVALKR (SEQ ID NO:6) of the two X region peptides correspond to amino acids 115-129 of FGF-2 identified by Ray et al. (Proc. Natl. Acad. Sci. USA 94:7047-7052, 1997).

The crude preparation was purified as described above in Example 1.

Example 3

Figure 3:
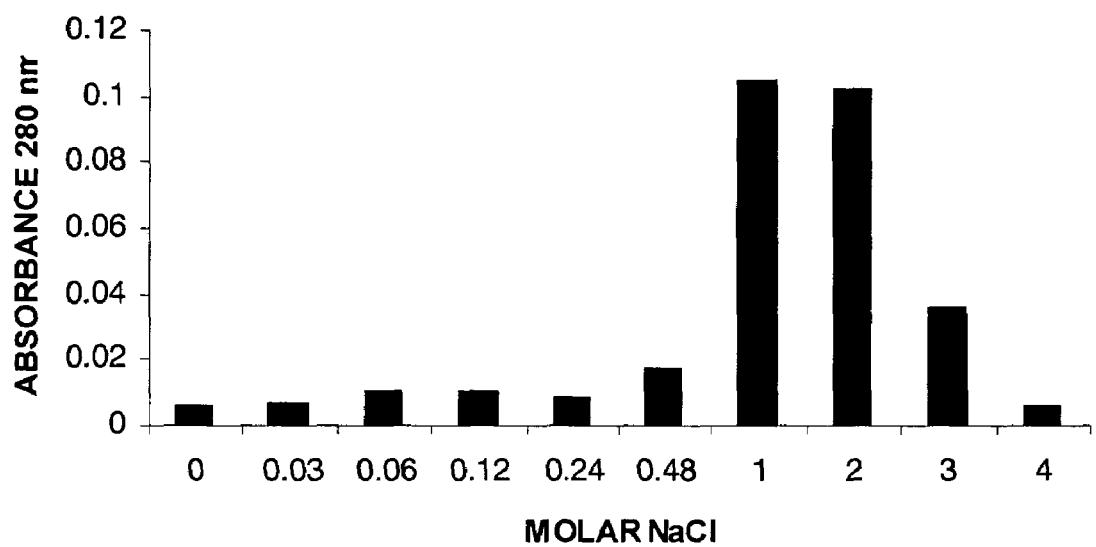
FIG. 3 is a plot of the elution of F2A3 from a heparin affinity column.

FIG. 3 shows the elution profile of F2A3 from a heparin affinity column. Mini columns were prepared with 0.5 mL heparin-agarose and washed extensively with water. F2A3 was loaded onto the column and rinsed with water. F2A3 was eluted from the column by stepwise increasing concentrations of NaCl as shown.

Example 4

Figure 4A:
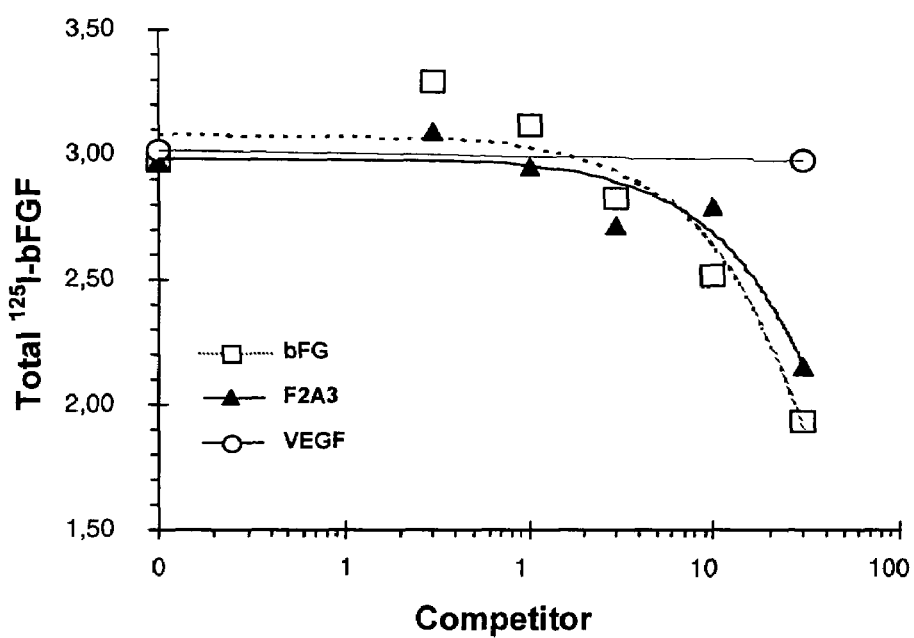
FIG. 4A is a graph depicting specific binding of F2A3 to FGFRs on HUVECs.
Figure 4B:
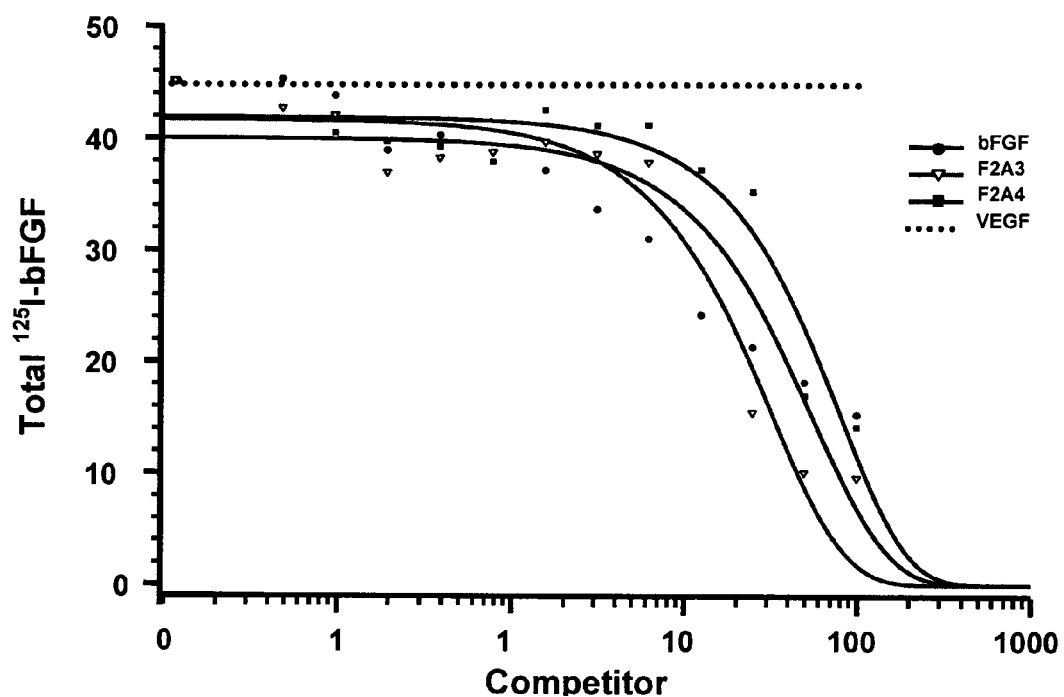
FIG. 4B is a graph depicting specific binding of F2A3 and F2A4 to FGFRs on C3H10T1/2 fibroblasts.

FIG. 4A shows the specific binding of F2A3 to HUVECs (Human umbilical vein endothelial cells). $^{125}$I-bFGF was incubated with intact HUVECs in the presence of unlabeled F2A3. The bound $^{125}$I-bFGF fraction at 4° C. was recovered from solubilized HUVEC membranes after stringent washing and quantitated in a gamma counter. F2A3 displaced $^{125}$I-bFGF (FGF-2) bound to FGF receptors of the HUVECs, while the unrelated heparin-binding cytokine, VEGF did not. FIG. 4B shows that F2A3 and F2A4 competitively displaced $^{125}$I-bFGF binding to a second series of cells containing FGF receptors, while the unrelated heparing-binding cytokine VEGF did not. $^{125}$I-bFGF was incubated with cultured C3H10T1/2 fibroblasts in the presence of cold F2A3 and F2A4 for 20 minutes on ice. After stringent washing, the bound $^{125}$I-bFGF fraction at 4° C. was recovered from solubilized cell membranes and quantitated in a gamma counter.

Example 5

Figure 5:
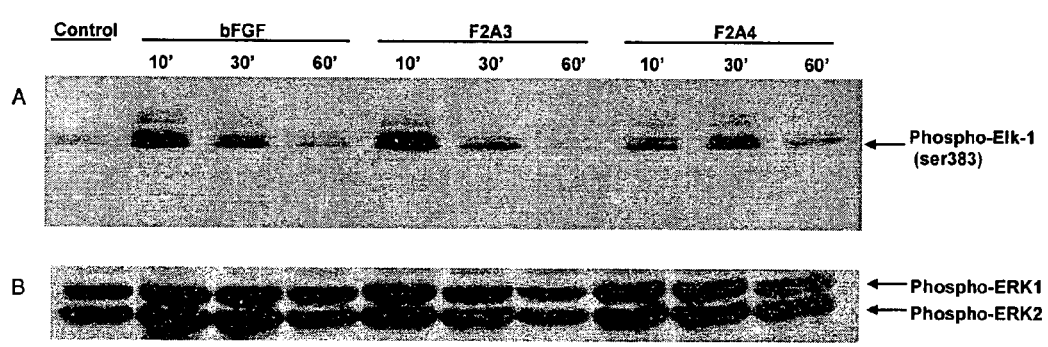
FIG. 5 is a blot illustrating the equivalence of FGF-2 analogs F2A3 and F2A4 to native, recombinant FGF-2 in MAP kinase phosphorylation and activation.

FIG. 5 shows the equivalence of FGF-2 analogs F2A3 and F2A4 to native, recombinant FGF-2 in MAP kinase phosphorylation and activation. C3H10T1/2 cells were stimulated with 3 nM of FGF-2, F2A3 or F2A4 for 10, 30 or 60 minutes and lysed. Active MAP kinase from cell lysates were immunoprecipitated with monoclonal anti-phosphop-44/42 MAP kinase (Thr202 and Tyr204). The resulting immunoprecipitate was incubated with an Elk-1 fusion protein in the presence of ATP. Phosphorylated Elk-1 at Ser383 was visualized by western blotting using a phosphor-Elk-1 (Ser 383) antibody. To reveal the phosphorylation of MAP kinase, cell lysates were analyzed by western blotting using monoclonal anti-phosphop-44/42 MAP kinase (Thr202 and Tyr204) antibody. The results show that both F2A3 and F2A4 activate Elk-1, as does FGF-2, as shown by the phosphorylated Ser383 residue present in these samples at 10 minutes and absent from the untreated control. The level of phosphorylated Ser383 decreased successively from 10 minutes to 30 minutes and even further at 60 minutes. By contrast, the level of phosphor-ERK-1 and phosphor-ERK-2 was consistently high in the F2A3, F2A4 and FGF-2 treated samples at 10 minutes, 30 minutes and 60 minutes, whereas the control untreated sample exhibited a distinguishably lower level of each of phosphor-ERK-1 and phosphor-ERK-2. These observations show that the HBGF analogs, F2A3 and F2A4 are biologically active as FGF-2 analogs in these assays.

Example 6

Figure 6:
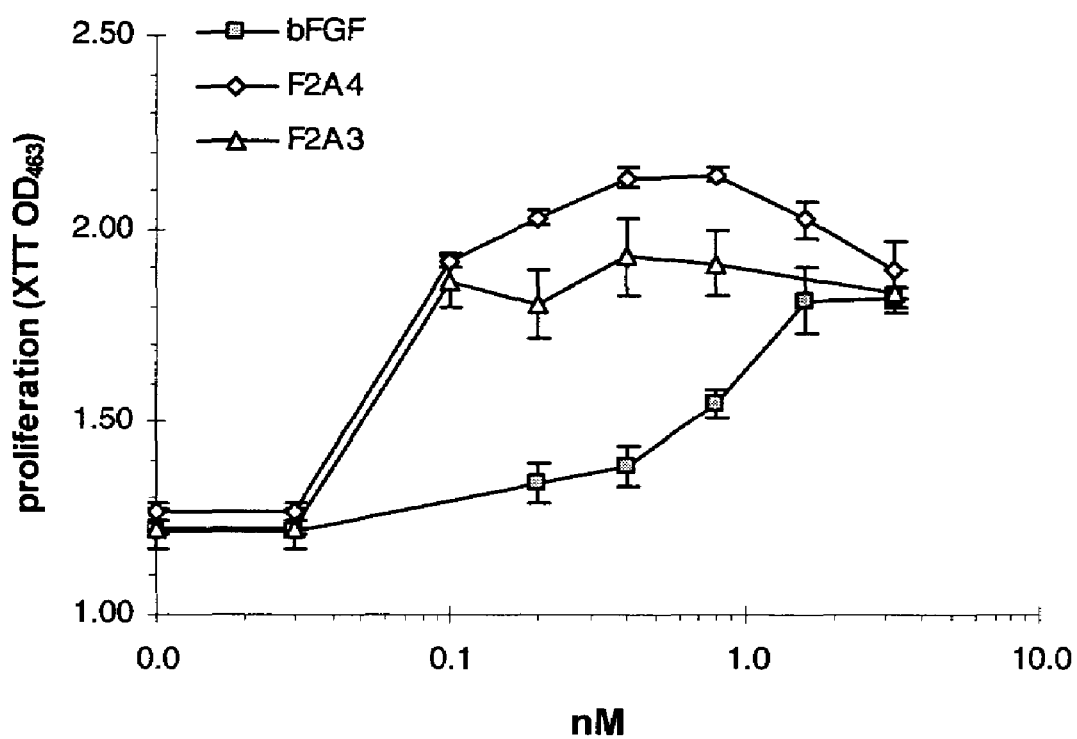
FIG. 6 is a graph of stimulation of cell proliferation in fibroblast cultures, illustrating the mitogenic dose response of F2A3 and F2A4 versus FGF-2.

FIG. 6 shows the results of an assay for mitogenesis by F2A3 and F2A4 as compared with bFGF (FGF-2). C3H10T1/2 cells were grown in DMEM medium supplemented with 10% FBS (fetal bovine serum). Two days before the assay, cell culture medium was replaced with low serum medium (DMEM with 0.1% FBS). At the start of the assay, cells were trypsinized and a single-cell suspension was seeded onto 96-well culture plates at 1,000 cells/well. Synthetic cytokine analog peptide or recombinant human FGF-2 were added to triplicate wells (100 µL/well final volume), and culture plates were returned to a 37° C. incubator. After three days, cell proliferation was quantified by the XTT Cell Proliferation Kit II (Roche Applied Science, Indianapolis, Ind., USA) according to manufacturer's instructions.

The analogs F2A3 and F2A4 provide higher specific activities at lower concentrations than FGF-2 as shown by the results of this assay.

Example 7

Figure 7A:
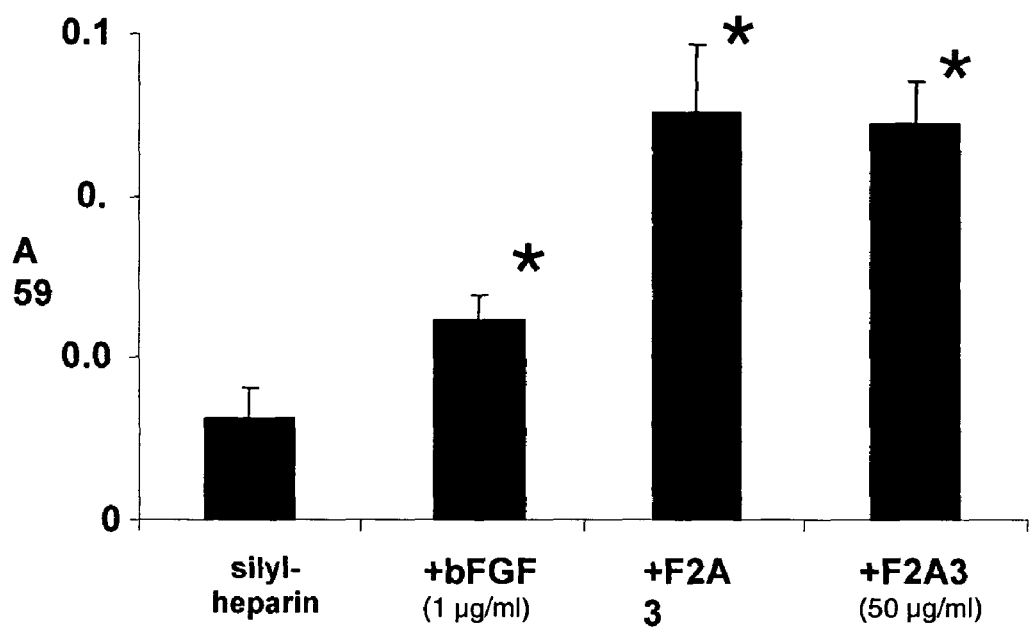
FIG. 7A is a plot illustrating that F2A3 and F2A4 mimic FGF-2 for cell attachment in vitro, showing attachment, after two hours, of CH310T1/2 murine fibroblasts to polystyrene coated with silyl-heparin alone or with silyl-heparin plus FGF-2 or F2A3. (*) indicates p less than 0.05.
Figure 7B:
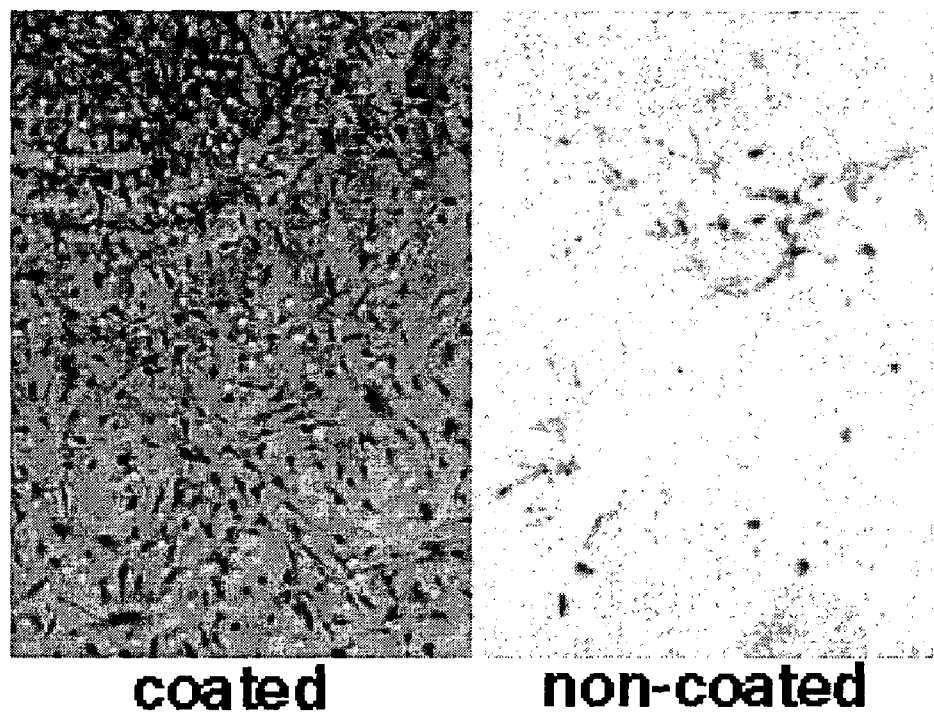
FIG. 7B is a micrograph of bovine aortic endothelial cells grown on polycaprolactone with (left panel) and without (right panel) a coating of F2A3.

FIG. 7 shows enhancement of attachment in vitro by F2A3. Attachment of C3H10T1/2 murine fibroblasts to the wells of a polystyrene 96-well tissue culture plate coated with silyl-heparin alone or with silyl-heparin plus bFGF (FGF-2) or silyl-heparin plus F2A3 at the indicated concentrations was measured by absorbance at 595 nm after 2 hours.

Micrographs of bovine aortic endothelial cells (BEACs) grown on polycaprolactone with or without a coating of F2A3 were obtained. Cells were stained with crystal violet and photographed at 100× magnification. A substantially higher cell density of attached cells on the F2A3 coated specimen was observed.

Example 8

Figure 8A:
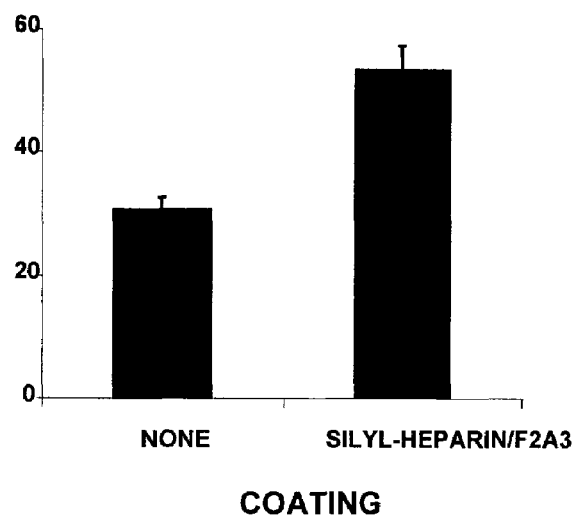
FIG. 8A is a plot illustrating the comparison of capillaries/ field utilizing coated polylactide sutures in rat muscle at 2 weeks, comparing no coating with sutures coated with silyl heparin plus F2A3.
Figure 8B:
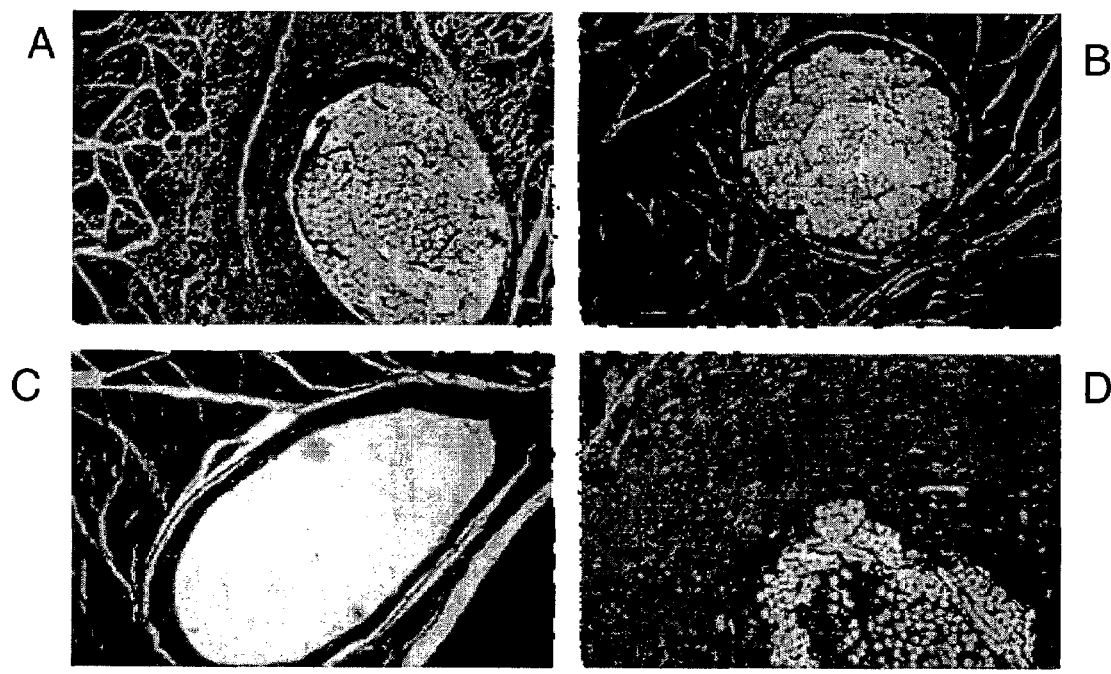
FIG. 8B are micrographs of coated polylactide sutures in rat muscle at 2 weeks, where panel A is no coating, panel B a silyl heparin coating, panel C F2A3 coating, and panel D, silyl heparin and F2A3 coating.

FIG. 8 shows the promotion of wound healing by locoregional delivery of F2A3 on biodegradable sutures. Bioabsorbable Vicryl® polyglycolide/lactide sutures (Ethicon Johnson & Johnson, Somerville, N.J., USA) coated to saturation with a combination silyl-heparin and F2A3 and without any coating were introduced into the thigh muscle of adult rats. After two weeks the implanted area was removed and processed for histology by routine methods. The capillaries were quantitated at a magnification of 100× and the data expressed as the average per field; as shown in FIG. 8, the Y axis depicts the number of capillaries per field. Increased granulation and angiogenesis were also observed utilizing H&E stained histological sections. Microscopic examination revealed a moderate amount of granulation after 2 weeks of rat muscle tissue where an uncoated suture was introduced. With both silyl-heparin coated sutures and F2A3 coated sutures, low to moderate granulation was found. With sutures coated with silyl-heparin and F2A3, braided PGLA fibers were evident in cross section, surrounded by a ring of granulation tissue of varying thickness, within a field of striated muscle tissue. Both silyl-heparin alone and F2A3 alone coatings reduced cellularity, compared to the control. But the combination of silyl-heparin and F2A3 caused marked fibroblast proliferation surrounding and infiltrating the braided suture, and increased endothelial cells within the granulation tissue.

Example 9

Figure 9:
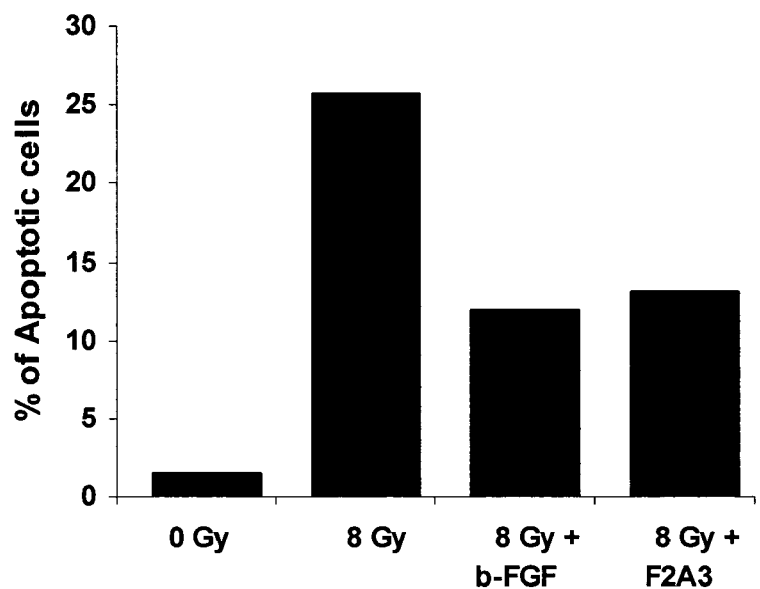
FIG. 9 is a plot illustrating radiation protection in endothelial cell cultures, with apoptosis induced by 8 Gy x-ray irradiation reduced by 50 ng/mL FGF-2 or F2A3.

FIG. 9 shows the results of a radiation protection experiment in which endothelial cells in culture were irradiated and the percent apoptotic cells measured after treatment with FGF-2 or F2A3 as compared to untreated controls. Apoptosis was induced by 8 Gy x-ray irradiation and treatment was with 50 ng/mL FGF-2 or F2A3.

Example 10

Figure 10:
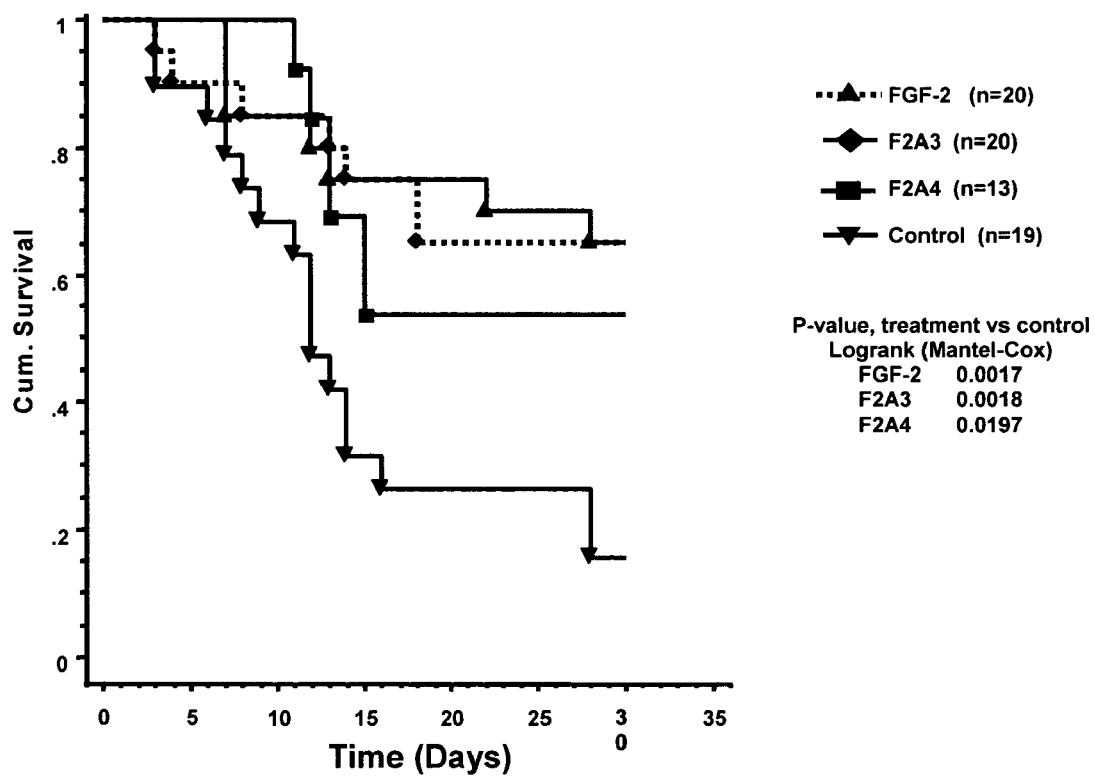
FIG. 10 is a plot showing radioprotection from G.I. syndrome in vivo, utilizing F2A3 and F2A4, with FGF-2 as a control.

FIG. 10 shows in vivo radioprotection from gastrointestinal syndrome death by F2A3 and F2A4 compared to bFGF (FGF-2) in the model mouse model developed by Ding & Okunieff (Okunieff et al., Br. J. Cancer. Suppl., 27:S105-8, (1996)). Immediately prior to whole body irradiation, adult C57BLxDBA mice were anesthetized by i.p. xylazine/ketamine injection. Subjects were administered, by i.v. retro-orbital injection, either 15 μg/mouse of FGF-2 (R&D Systems, Minneapolis, Minn., USA), 5 μg/mouse of F2A3, 5 μg/mouse F2A4, or control vehicle solution (100 μL of 0.2% gelatin in 0.9% NaCl), and then subjected to 14 Gy gamma-irradiation by a $^{137}$Cs source (dose rate 0.93 Gy/min). Animals were monitored twice daily for 30 days, and statistical analysis of survival data was done by the method of Kaplan-Meier.

Example 11

A synthetic HBGF analog, F1A1, was synthesized by standard solid phase peptide synthesis methods. The amino acid sequences of F1A1 corresponding to regions Y and Z of formula II are identical to those of F2A3 described in Example 1. The FGF receptor binding amino acid sequence of the two X region sequences is YISKKHAEKN-WFVGLKK (SEQ ID NO:8). This sequence is derived from amino acids bridging the beta 9 and beta 10 loop of FGF-1.

The crude preparation was purified as described above in Example 1. The resulting analog had the following structure:

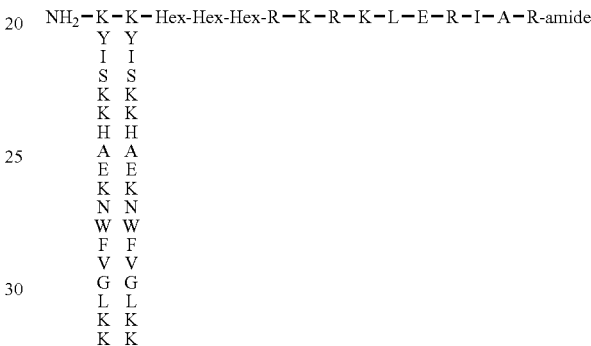

Example 12

A synthetic HBGF analog, F1A2, was synthesized by standard solid phase peptide synthesis methods. The amino acid sequences of F1A2 corresponding to regions Y and Z of formula II are identical to those of F2A3 described in Example 1. The amino acid sequence HIQLQLSASEV-GEVY (SEQ ID NO:9) of the two X region peptides corresponds to amino acids derived from the β-4 and β-5 region of FGF-1. This general region is implicated in the binding of FGF-1 (Sanz, et al. Hints of nonhierarchical folding of acidic fibroblast growth factor. Biochemistry 41:1923-1933 (2002)).

The crude preparation was purified as described above in Example 1. The resulting analog had the following structure:

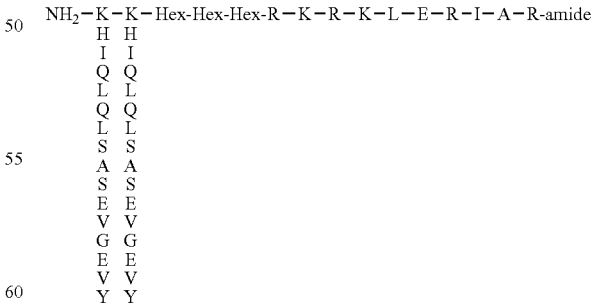

Example 13

A synthetic HBGF analog, F7A1, was synthesized by standard solid phase peptide synthesis methods. The amino acid sequences of F7A1 corresponding to regions Y and Z of formula II are identical to those of F2A3 described in Example 1. The amino acid sequence YASAKWTH-NGGEMFVALNQK (SEQ ID NO:10) of the two X region peptides corresponds to amino acids derived from the beta 9 and beta 10 loop of FGF-7. Residues 91-110 which are included in this segment of FGF-7 have been described as being important for determining specificity for FGFR2IIb Kim et al. (Kim et al. Colocalization of heparin and receptor binding sites on keratinocyte growth factor. Biochemistry 37:8853-8862 (1998)).

The crude preparation was purified as described above in Example 1. The resulting analog had the following structure:

NH₂−K−K−Hex-Hex-Hex-R−K−R−K−L−E−R−I−A−R-amide
          Y Y
          A A
          S S
          A A
          K K
          W W
          T T
          H H
          N N
          G G
          G G
          E E
          M M
          F F
          V V
          A A
          L L
          N N
          Q Q
          K K Example 14

A synthetic HBGF analog, F7A2, was synthesized by standard solid phase peptide synthesis methods. The amino acid sequences of F7A2 corresponding to regions Y and Z of formula II are identical to those of F2A3 described in Example 1. The amino acid sequence YNIMEIRTVAVGIVA (SEQ ID NO:11) of the two X region peptides corresponds to amino acids derived from the β-4 and β-5 region of FGF-7. The loop connecting the β-4-β5 strands of FGF-7 contribute to high affinity receptor binding and is critical for FGFR recognition, as determined in domain-swapping and site-directed mutagenesis experiments (Sher et al. Identification of residues important both for primary receptor binding and specificity in fibroblast growth factor-7. J Biol. Chem. 275: 34881-34886 (2000)).

The crude preparation was purified as described above in Example 1. The resulting analog had the following structure:

NH₂−K−K−Hex-Hex-Hex-R−K−R−K−L−E−R−I−A−R-amide
          Y Y
          N N
          I I
          M M
          E E
          I I
          R R
          T T
          V V
          A A
          V V
          G G
          I I
          V V
          A A Example 15

A synthetic HBGF analog, VA01, was synthesized by standard solid phase peptide synthesis methods. The amino acid sequences of VA01 corresponding to regions Y and Z of formula II are identical to those of F2A3 described in Example 1. The amino acid sequence APMAEGGGQNH-HEVVKFMDV (SEQ ID NO:12) of the two X region peptides was derived from the first 20 amino acids of the VEGF sequence as described by Binetruy-Tournaire et al. (Binetruy-Tournaire et al., Identification of a peptide blocking vascular endothelial growth factor (VEGF)-mediated angiogenesis. Embo. J. 19:1525-1533 (2000)).

The crude preparation was purified as described above in Example 1. The resulting analog had the following structure:

NH₂−K−K−Hex-Hex-Hex-R−K−R−K−L−E−R−I−A−R-amide
          A A
          P P
          M M
          A A
          E E
          G G
          G G
          G G
          Q Q
          N N
          H H
          H H
          E E
          V V
          V V
          K K
          F F
          M M
          D D
          V V Example 16

A synthetic HBGF analog, VA02, was synthesized by standard solid phase peptide synthesis methods. The amino acid sequences of VA02 corresponding to regions Y and Z of formula II are identical to those of F2A3 described in Example 1. The amino acid sequence GATWLPPNPTK (SEQ ID NO:13) of the two X region peptides has never explicitly been described or characterized in the scientific literature, but rather was derived from shorter sequences described by Binetruy-Tournaire (Binetruy-Tournaire et al., Identification of a peptide blocking vascular endothelial growth factor (VEGF)-mediated angiogenesis. Embo. J. 19:1525-1533 (2000)).

The crude preparation was purified as described above in Example 1. The resulting analog had the following structure:

NH₂−K−K−Hex-Hex-Hex-R−K−R−K−L−E−R−I−A−R-amide
          G G
          A A
          T T
          W W
          L L
          P P
          P P
          N N
          P P
          T T
          K K Example 17

A synthetic HBGF analog, VEGF1-20, was synthesized by standard solid phase peptide synthesis methods. The amino acid sequences of VEGF1-20 corresponding to regions Y and Z of formula II are identical to those of F2A3 described in Example 1, with the X amino acid sequence NFLLSWVH-WSLALLLYLHHA (SEQ ID NO:14) forming a vascular endothelial growth factor sequence.

The crude preparation was purified as described above in Example 1.

Example 18

A synthetic HBGF analog, B2A1, was synthesized by standard solid phase peptide synthesis methods. The amino acid sequences of B2A1 corresponding to regions Y and Z of formula II are identical to those of F2A3 described in Example 1. The amino acid sequence LYVDFSDVGWNDW (SEQ ID NO:15) of the two X region peptides corresponds to amino acids 301-313 of BMP-2.

The crude preparation was purified as described above in Example 1.

Example 19

A synthetic HBGF analog, B2A2, was synthesized by standard solid phase peptide synthesis methods. The amino acid sequences of B2A2 corresponding to regions Y and Z of formula II are identical to those of F2A3 described in Example 1. The amino acid sequence AISM-LYLDENEKVVL (SEQ ID NO:16) of the two X region peptides corresponds to amino acids 91-105 of the strands beta 7 and beta 8 in BMP-2. This region is thought to be part of the epitope 2 of BMP-2 that is involved in binding of BMPR-II.

The crude preparation was purified as described above in Example 1.

Example 20

A synthetic HBGF analog, B2A2-1.2, is synthesized by standard solid phase peptide synthesis methods. The amino acid sequences of B2A2-1.2 corresponding to regions Y and Z of forula II is identical to those of F2A3 described in Example 1. The amino acid sequence ISMLYLDENEKVV-LKNY (SEQ ID NO:17) of the two X region peptides corresponds to amino acids found in the beta 7 and beta 8 region of BMP-2.

The crude preparation is purified as described above in Example 1.

Example 21

A synthetic HBGF analog, B2A2-1.4E, is synthesized by standard solid phase peptide synthesis methods. The amino acid sequences of B2A2-1.4E corresponding to regions Y and Z of formula II is identical to those of F2A3 described in Example 1. The amino acid sequence EKVVLKNYODM-VVEG (SEQ ID NO:18) of the two X region peptides corresponds to amino acids found in the beta 8 region of BMP-2.

The crude preparation is purified as described above in Example 1.

Example 22

A synthetic HBGF analog, B2A3, is synthesized by standard solid phase peptide synthesis methods. The amino acid sequences of B2A3 corresponding to regions Y and Z of formula II is identical to those of F2A3 described in Example 1. The amino acid sequence LVVKENEDLYLMSIAC (SEQ ID NO:19) of the two X region peptides corresponds to amino acids found in the beta 8 region of BMP-2.

The crude preparation is purified as described above in Example 1.

Example 23

A synthetic HBGF analog, B2A4-1.1, is synthesized by standard solid phase peptide synthesis methods. The amino acid sequences of B2A4-1.1 corresponding to regions Y and Z of formula II is identical to those of F2A3 described in Example 1. The amino acid sequence AFYCHGECPFP-LADHL (SEQ ID NO:20) of the two X region peptides corresponds to amino acids found in the beta 4 and beta 5 region of BMP-2.

The crude preparation is purified as described above in Example 1.

Example 24

A synthetic HBGF analog, B2A4-1.3, is synthesized by standard solid phase peptide synthesis methods. The amino acid sequences of B2A4-1.3 corresponding to regions Y and Z of formula II are identical to those of F2A3 described in Example 1. The amino acid sequence PFPLADHLNST-NHAIVQTLVNSV (SEQ ID NO:21) of the two X region peptides corresponds to amino acids found in the beta 5 and beta 5a region of BMP-2.

The crude preparation is purified as described above in Example 1.

Example 25

A synthetic HBGF analog, F2A4-Lin, was synthesized by standard solid phase peptide synthesis methods. This analog was a linear peptide of the amino acid sequence $NH_2$-YRSRKYSSWYVALKRT-HexHexHex-RKRKLERIAR-amide (SEQ ID NO:22), which is a peptide of formula I, wherein n=0, T is $R_1$, X is YRSRKYSSWYVALKR (SEQ ID NO:6) and Z is SEQ ID NO:2, with X and Z covalently bonded by a peptide bond. The crude preparation was purified as described above in Example 1.

Example 26

A synthetic HBGF analog, F2A4-Sin, was synthesized by standard solid phase peptide synthesis methods. This analog is a single chain branched peptide of formula II, wherein n=0, $J_1$ is Lys, X is SEQ ID NO:6, Z is SEQ ID NO:2 and Y is Hex-Hex-Hex, with X covalently bonded by an amide bond to the side chain of $J_1$, of the following structure:

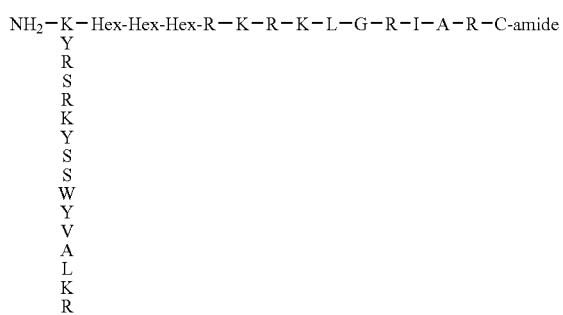

Example 27

Figure 11:
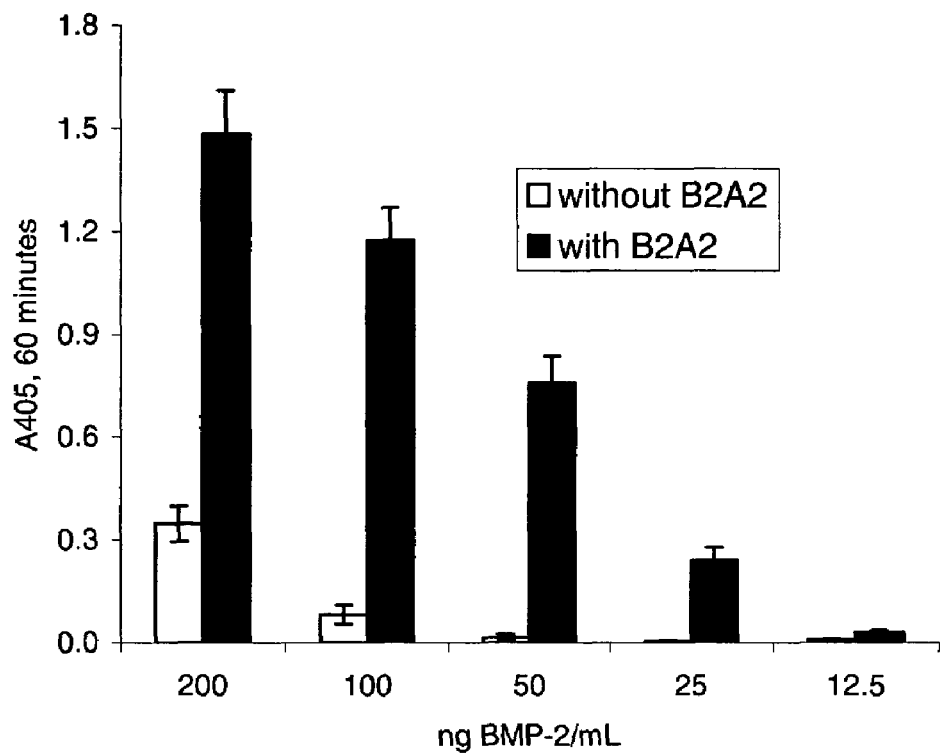
FIG. 11 is a plot illustrating induction of alkaline phosphatase in murine C2C12 cells at different concentrations of BMP-2 with and without B2A2.

This example demonstrates positive modulation of B2A2 on the induction of alkaline phosphatase in murine C2C12 cells. Cells were seeded at $10^4$ cells/well in 96 well plates, incubated for 1 day in medium containing 10% newborn calf serum, changed to a medium containing 2% serum with or recombinant BMP-2 (*E. coli*), and incubated for 3 additional days. B2A2, when used, was added to a final concentration of 1000 ng/mL. Alkaline phosphatase was measured following a 10 minute fix in 1% buffered formalin, incubation in 0.3% Triton X 100, with chromogen development for 60 minutes using a commercially available para-nitrophenol (PNPP) kit. Data, as shown in FIG. 11, was expressed as the average ±S.D., where n=5. Induction of alkaline phosphatase is characteristic for the biological activity of BMP-2.

Example 28

Figure 12:
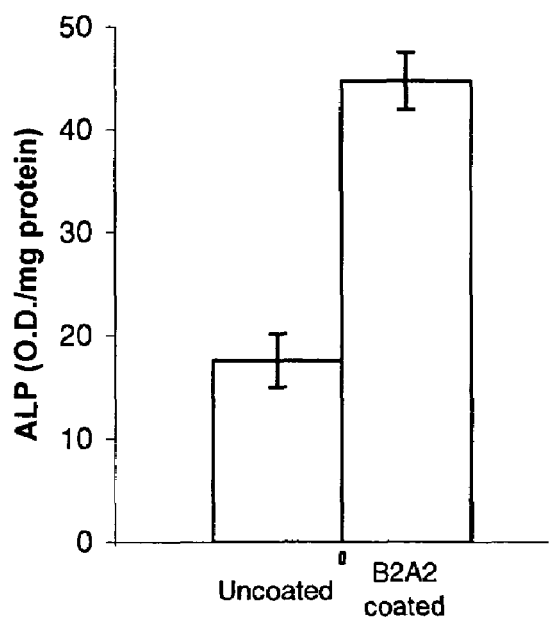
FIG. 12 is a plot illustrating positive modulation of BMP-2 by B2A2 on C3H10T1/2 murine cells, comparing uncoated cells to B2A2 coated cells, with detection by alkaline phosphates.

This example demonstrates positive modulation of BMP-2 activity by B2A2 when used as a coating. Wells of 96-well plates were pre-coated using 60% aqueous isopropanol containing 0.25% silyl-heparin [benzyl-tetra(dimethylsilylmethyl) oxycarbamoyl-heparin] followed by rinsing in water to remove unbound material. Wells were then treated with water (control) or with an aqueous solution containing 10 μg/mL of B2A2. After removal of the treatment solution aliquots of $2 \times 10^4$ C3H10T1/2 murine cells were added in a volume of 100 μL followed by the addition of 10 ng of recombinant BMP-2 (*E. coil*) in 5 μL. After several days the cultures were evaluated for the alkaline phosphates (ALP) activity and for the amount of total protein. The data, as shown in FIG. 12, was expressed as the average optical density obtained from the ALP assay over the amount of protein in mg.

Example 29

Figure 13:
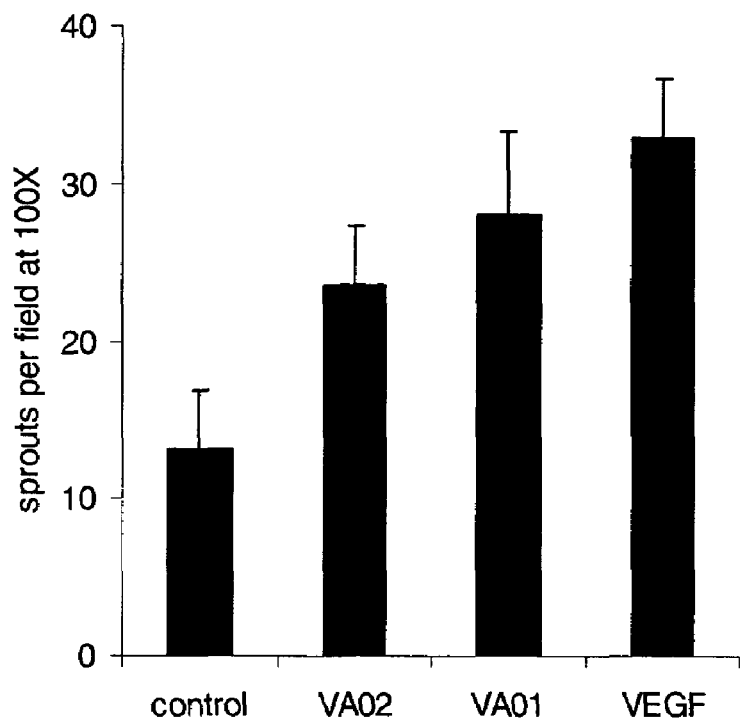
FIG. 13 is a plot of sprouts induced in bovine aorta endothelial cells as a result of addition of VA01, VA02 or recombinant VEGF.

This example demonstrates the effect of VEGF mimetic peptides in an in vitro model of angiogenesis. Bovine aorta endothelial cells were seeded in individual wells of 96 well plates containing a layer of collagen gel. The cells were allowed to attach to the gel and unbound cells subsequently removed. The attached cells were covered with a second layer of collagen gel containing either no addition (control) or 25 ng/mL of VA01, VA02, or recombinant VEGF. After the second layer of gel had hardened, the culture was overlayered with 100 μL of medium containing the test materials at the concentrations specified above. After several days the cultures were examined by phase contrast microscopy and the number of sprouts invading the gel was recorded. The data was expressed the average ±S.D., where n=6. The results are shown in FIG. 13. The ability of agents to stimulate sprouting is an accepted predictive model of in vivo angiogenesis.

Example 30

Figure 14:
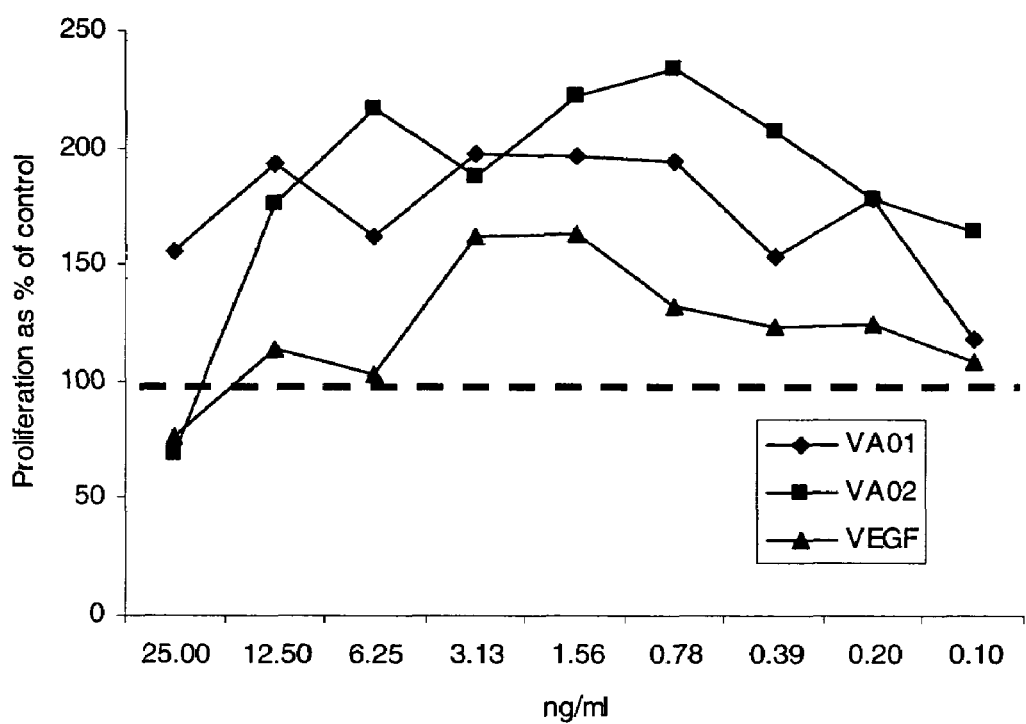
FIG. 14 is plot of stimulation of growth of bovine aorta endothelial (BAE) cells with VA01, VA02 and VEGF.

This example demonstrates stimulation of growth of bovine aorta endothelial (BAE) cells by VA01 and VA02 at 48 hours after addition to the medium. Aliquots of $10^3$ BAE cells were seeded into wells of 96 well plates and allowed 24 hours to attach to the substrate. The medium was then changed to one containing 2% newborn calf serum that contained no addition (control) or VA01, VA02, or recombinant VEGF at the concentrations indicated above. After 48 hours the cells were assayed using a commercially available XTT kit as in Example 6. The absorbance was expressed as a percentage of control values. VEGF generated a modest increase in growth over a limited concentration range while VA01 and VA02 had more pronounced growth stimulation over a broader concentration range, as shown in FIG. 14. The dotted line indicates the control value.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

We claim:

1. A heparin-binding growth factor (HBGF) analog of formula II:

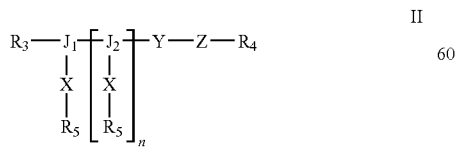

wherein:

$R_3$ and $R_5$ are each independently $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, NH group or a corresponding acylated derivative, or is an amino acid, a dipeptide or a tripeptide with an N-terminus $NH_2$, $NH_3^+$, NH group or a corresponding acylated derivative;

$R_4$ is —OH, $NH_2$, NH—$R_6$, or is an amino acid, a dipeptide or a tripeptide with a C-terminus —OH, $NH_2$, or NH—$R_6$;

$R_6$ is an aliphatic $C_1$ to $C_{17}$ chain;

each X comprises a peptide chain that is selected from SEQ ID NO: 6, SEQ ID NO:10, SEQ ID NO:14, SEQ ID NO:16, SEQ ID NO:17, SEQ ID NO:18, and SEQ ID NO:19;

$J_1$ and $J_2$ are each independently a trifunctional alpha amino acid residue, wherein each X is covalently bonded through a side chain of $J_1$ or $J_2$;

Y is a linker comprising three amino hexanoic acid residues;

Z is a non-signaling peptide that comprises a heparin binding domain, comprising SEQ ID NO: 2;

n is 0 or 1, wherein when n=1 the synthetic peptide chains X are identical.

2. The heparin-binding growth factor analog of claim 1 wherein X and Z are synthetic peptide chains.

3. The heparin-binding growth factor analog of claim 1 wherein the heparin-binding growth factor analog has an avidity for heparin such that the heparin-binding growth factor analog binds heparin in 0.15 M NaCl, but is eluted by 1 M NaCl.

4. The heparin-binding growth factor analog of claim 1 wherein $J_1$ is, and if n=1, $J_1$ and $J_2$ is a diamine amino acid residue.

5. The heparin-binding growth factor analog of claim 4 wherein the diamine amino acid residue is a 2,3 diamino propionyl amino acid residue.

6. The heparin-binding growth factor analog of claim 4 wherein the diamine amino acid residue is lysine.

7. The heparin-binding growth factor analog of claim 4 wherein the diamine amino acid residue is ornithine.

8. The heparin-binding growth factor analog of claim 1 wherein the covalent bond between X and $J_1$ or, if n=1, $J_1$ and $J_2$, comprises a peptide, disulfide, thioether, Schiff base, reduced Schiff base, imide, secondary amine, carbonyl, urea, hydrazone or oxime bond.

9. The heparin-binding growth factor analog of claim 1 wherein the side chain of $J_1$ and, if n=1, $J_1$ and $J_2$, comprises a reactive carboxyl group.

10. The heparin-binding growth factor analog of claim 1 wherein the heparin-binding growth factor analog binds an FGF receptor.

11. The heparin-binding growth factor analog of claim 1 wherein the peptide chains X are cross-linked or cyclized.

12. The heparin-binding growth factor analog of claim 11 wherein the peptide chains X are cross-linked or cyclized by at least one disulfide, peptide, or thioether bond.

* * * * *

SEQUENCE LISTING

```
<160> NUMBER OF SEQ ID NOS: 22

<210> SEQ ID NO 1
<211> LENGTH: 6
<212> TYPE: PRT
<213> ORGANISM: Artificial
<220> FEATURE:
<223> OTHER INFORMATION: Heparin-binding motif
<220> FEATURE:
<221> NAME/KEY: misc_feature
<222> LOCATION: (1)..(3)
<223> OTHER INFORMATION: LYS or ARG
<220> FEATURE:
<221> NAME/KEY: misc_feature
<222> LOCATION: (4)..(5)
<223> OTHER INFORMATION: any amino acid
<220> FEATURE:
<221> NAME/KEY: misc_feature
<222> LOCATION: (6)..(6)
<223> OTHER INFORMATION: LYS or ARG

<400> SEQUENCE: 1

Xaa Xaa Xaa Xaa Xaa Xaa
1               5
```

<210> SEQ ID NO 2
<211> LENGTH: 10
<212> TYPE: PRT
<213> ORGANISM: Artificial
<220> FEATURE:
<223> OTHER INFORMATION: Heparin-binding domain of Z region

<400> SEQUENCE: 2

Arg Lys Arg Lys Leu Glu Arg Ile Ala Arg
1               5                   10

<210> SEQ ID NO 3
<211> LENGTH: 10
<212> TYPE: PRT
<213> ORGANISM: Artificial
<220> FEATURE:
<223> OTHER INFORMATION: Heparin-binding domain of Z region

<400> SEQUENCE: 3

Arg Lys Arg Lys Leu Gly Arg Ile Ala Arg
1               5                   10

<210> SEQ ID NO 4
<211> LENGTH: 10
<212> TYPE: PRT
<213> ORGANISM: Artificial
<220> FEATURE:
<223> OTHER INFORMATION: Heparin-binding domain of Z region

<400> SEQUENCE: 4

Arg Lys Arg Lys Leu Trp Arg Ala Arg Ala
1               5                   10

<210> SEQ ID NO 5
<211> LENGTH: 11
<212> TYPE: PRT
<213> ORGANISM: Artificial
<220> FEATURE:
<223> OTHER INFORMATION: Heparin-binding domain of Z region

<400> SEQUENCE: 5

Arg Lys Arg Lys Leu Glu Arg Ile Ala Arg Cys
1               5                   10

<210> SEQ ID NO 6
<211> LENGTH: 15
<212> TYPE: PRT
<213> ORGANISM: Artificial
<220> FEATURE:
<223> OTHER INFORMATION: Synthetic FGF-2 analog -continued

```
<210> SEQ ID NO 8
<211> LENGTH: 17
<212> TYPE: PRT
<213> ORGANISM: Artificial
<220> FEATURE:
<223> OTHER INFORMATION: Synthetic FGF-1 analog

<400> SEQUENCE: 8

Tyr Ile Ser Lys Lys His Ala Glu Lys Asn Trp Phe Val Gly Leu Lys
1               5                   10                  15

Lys

<210> SEQ ID NO 9
<211> LENGTH: 15
<212> TYPE: PRT
<213> ORGANISM: Artificial
<220> FEATURE:
<223> OTHER INFORMATION: Synthetic FGF-1 analog

<400> SEQUENCE: 9

His Ile Gln Leu Gln Leu Ser Ala Ser Glu Val Gly Glu Val Tyr
1               5                   10                  15

<210> SEQ ID NO 10
<211> LENGTH: 20
<212> TYPE: PRT
<213> ORGANISM: Artificial
<220> FEATURE:
<223> OTHER INFORMATION: Synthetic FGF-7 analog

<400> SEQUENCE: 10

Tyr Ala Ser Ala Lys Trp Thr His Asn Gly Gly Glu Met Phe Val Ala
1               5                   10                  15

Leu Asn Gln Lys
            20

<210> SEQ ID NO 11
<211> LENGTH: 15
<212> TYPE: PRT
<213> ORGANISM: Artificial
<220> FEATURE:
<223> OTHER INFORMATION: Synthetic FGF-7 analog

<400> SEQUENCE: 11

Tyr Asn Ile Met Glu Ile Arg Thr Val Ala Val Gly Ile Val Ala
1               5                   10                  15

<210> SEQ ID NO 12
<211> LENGTH: 20
<212> TYPE: PRT
<213> ORGANISM: Artificial
<220> FEATURE:
<223> OTHER INFORMATION: Synthetic VEGF analog

<400> SEQUENCE: 12

Ala Pro Met Ala Glu Gly Gly Gly Gln Asn His His Glu Val Val Lys
1               5                   10                  15

Phe Met Asp Val
            20

<210> SEQ ID NO 13
<211> LENGTH: 11
<212> TYPE: PRT
<213> ORGANISM: Artificial
<220> FEATURE:
<223> OTHER INFORMATION: Synthetic VEGF analog
```

```
<400> SEQUENCE: 13

Gly Ala Thr Trp Leu Pro Pro Asn Pro Thr Lys
1               5                   10

<210> SEQ ID NO 14
<211> LENGTH: 20
<212> TYPE: PRT
<213> ORGANISM: Artificial
<220> FEATURE:
<223> OTHER INFORMATION: Synthetic VEGF analog

<400> SEQUENCE: 14

Asn Phe Leu Leu Ser Trp Val His Trp Ser Leu Ala Leu Leu Leu Tyr
1               5                   10                  15

Leu His His Ala
            20

<210> SEQ ID NO 15
<211> LENGTH: 13
<212> TYPE: PRT
<213> ORGANISM: Artificial
<220> FEATURE:
<223> OTHER INFORMATION: Synthetic BMP analog

<400> SEQUENCE: 15

Leu Tyr Val Asp Phe Ser Asp Val Gly Trp Asn Asp Trp
1               5                   10

<210> SEQ ID NO 16
<211> LENGTH: 15
<212> TYPE: PRT
<213> ORGANISM: Artificial
<220> FEATURE:
<223> OTHER INFORMATION: Synthetic BMP analog

<400> SEQUENCE: 16

Ala Ile Ser Met Leu Tyr Leu Asp Glu Asn Glu Lys Val Val Leu
1               5                   10                  15

<210> SEQ ID NO 17
<211> LENGTH: 17
<212> TYPE: PRT
<213> ORGANISM: Artificial
<220> FEATURE:
<223> OTHER INFORMATION: Synthetic BMP analog

<400> SEQUENCE: 17

Ile Ser Met Leu Tyr Leu Asp Glu Asn Glu Lys Val Val Leu Lys Asn
1               5                   10                  15

Tyr

<210> SEQ ID NO 18
<211> LENGTH: 15
<212> TYPE: PRT
<213> ORGANISM: Artificial
<220> FEATURE:
<223> OTHER INFORMATION: Synthetic BMP analog

<400> SEQUENCE: 18

Glu Lys Val Val Leu Lys Asn Tyr Gln Asp Met Val Val Glu Gly
1               5                   10                  15
```

-continued

```
<210> SEQ ID NO 19
<211> LENGTH: 16
<212> TYPE: PRT
<213> ORGANISM: Artificial
<220> FEATURE:
<223> OTHER INFORMATION: Synthetic BMP analog

<400> SEQUENCE: 19

Leu Val Val Lys Glu Asn Glu Asp Leu Tyr Leu Met Ser Ile Ala Cys
1               5                   10                  15

<210> SEQ ID NO 20
<211> LENGTH: 16
<212> TYPE: PRT
<213> ORGANISM: Artificial
<220> FEATURE:
<223> OTHER INFORMATION: Synthetic BMP analog

<400> SEQUENCE: 20

Ala Phe Tyr Cys His Gly Glu Cys Pro Phe Pro Leu Ala Asp His Leu
1               5                   10                  15

<210> SEQ ID NO 21
<211> LENGTH: 23
<212> TYPE: PRT
<213> ORGANISM: Artificial
<220> FEATURE:
<223> OTHER INFORMATION: Synthetic BMP analog

<400> SEQUENCE: 21

Pro Phe Pro Leu Ala Asp His Leu Asn Ser Thr Asn His Ala Ile Val
1               5                   10                  15

Gln Thr Leu Val Asn Ser Val
            20

<210> SEQ ID NO 22
<211> LENGTH: 29
<212> TYPE: PRT
<213> ORGANISM: Artificial
<220> FEATURE:
<223> OTHER INFORMATION: Synthetic heparin-binding growth factor analog
      specific for FGF-2 with heparin-binding region
<220> FEATURE:
<221> NAME/KEY: MISC_FEATURE
<222> LOCATION: (17)..(19)
<223> OTHER INFORMATION: 6-aminohexanoic acid

<400> SEQUENCE: 22

Tyr Arg Ser Arg Lys Tyr Ser Ser Trp Tyr Val Ala Leu Lys Arg Thr
1               5                   10                  15

Xaa Xaa Xaa Arg Lys Arg Lys Leu Glu Arg Ile Ala Arg
            20                  25
```